US010415043B2

(12) United States Patent
Koepke et al.

(10) Patent No.: US 10,415,043 B2
(45) Date of Patent: Sep. 17, 2019

(54) VITAMIN PROTOTROPHY AS A SELECTABLE MARKER

(71) Applicant: LanzaTech New Zealand Limited, Skokie, IL (US)

(72) Inventors: Michael Koepke, Skokie, IL (US); Bakir Al-Sinawi, Sydney (AU)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 0 days.

(21) Appl. No.: 15/285,179

(22) Filed: Oct. 4, 2016

(65) Prior Publication Data

US 2017/0016007 A1  Jan. 19, 2017

Related U.S. Application Data

(63) Continuation of application No. 13/900,172, filed on May 22, 2013, now abandoned.

(60) Provisional application No. 61/650,757, filed on May 23, 2012.

(51) Int. Cl.

| | |
|---|---|
| *C12N 15/65* | (2006.01) |
| *C12N 15/60* | (2006.01) |
| *C12N 15/54* | (2006.01) |
| *C12N 9/10* | (2006.01) |
| *C12N 9/88* | (2006.01) |
| *C12N 15/74* | (2006.01) |
| *C12N 15/52* | (2006.01) |
| *C12N 1/20* | (2006.01) |
| *C12N 9/00* | (2006.01) |

(52) U.S. Cl.
CPC ........... *C12N 15/65* (2013.01); *C12N 1/20* (2013.01); *C12N 9/1014* (2013.01); *C12N 9/88* (2013.01); *C12N 15/52* (2013.01); *C12N 15/74* (2013.01); *C12Y 201/02011* (2013.01); *C12Y 401/01011* (2013.01); *C12Y 401/99017* (2013.01); *C12N 9/93* (2013.01); *C12Y 202/01011* (2015.07); *C12Y 603/02001* (2013.01)

(58) Field of Classification Search
None
See application file for complete search history.

(56) References Cited

U.S. PATENT DOCUMENTS

| | | |
|---|---|---|
| 5,173,429 A | 12/1992 | Gaddy et al. |
| 5,593,886 A | 1/1997 | Gaddy et al. |
| 6,368,819 B1 | 4/2002 | Gaddy et al. |
| 2005/0089973 A1 | 4/2005 | Yocum et al. |
| 2006/0141585 A1 | 6/2006 | Yocum et al. |
| 2010/0304432 A1* | 12/2010 | O'Keefe ............ C07K 14/195 435/69.1 |
| 2010/0311104 A1 | 12/2010 | Simpson et al. |
| 2011/0229947 A1 | 9/2011 | Zahn et al. |
| 2011/0256600 A1 | 10/2011 | Simpson et al. |
| 2012/0107888 A1 | 5/2012 | Schmalisch et al. |
| 2012/0203018 A1 | 8/2012 | Franklin et al. |
| 2013/0078694 A1 | 3/2013 | Tao et al. |
| 2013/0244220 A1 | 9/2013 | Senaratne et al. |

FOREIGN PATENT DOCUMENTS

| | | |
|---|---|---|
| WO | 2002008438 | 1/2002 |
| WO | 2008028055 | 3/2008 |
| WO | 2009064200 | 5/2009 |
| WO | 2012015317 | 2/2012 |
| WO | 2012115527 | 8/2012 |

OTHER PUBLICATIONS

Kita et al., Development of genetic transformation and heterologous expression system in carboxydotrophic thermophilic acetogen Moorella thermoacetica, J. Biosci. Bioeng., 2013, 115, 347-52.*
Uniprot, Accession No. A0A1A6AW80, 2019, www.uniprot.org.*
Abrini, Arch Microbiol, 161: 345-351, 1994.
Begley, Arch Microbial, 171: 293-300, 1999.
Collins, Int J System Bacterial, 44: 812-826, 1994.
Drake, Prokaryotes, 2: 354-420, 2006.
Dürre, Species and Strain Identification Methods, Handbook on Clostridia, CRC press, pp. 3-4, 2005.
Heap, J Microbial Methods, 78: 79-85, 2009.
Herbert, FEMS Microbiol Lett, 229: 103-110, 2003.
Ismaiel, J Bacterial, 175: 5079-5105, 1993.
Jennert, Microbiol, 146: 3071-3080, 2000.
Kita, J Biosci Bioeng, 115: 347-352, 2013.
Köpke, Appl Environ Microbiol, 77: 5467-5475, 2011.
Köpke, Biochemical production of biobutanol, In: Handbook of biofuels production: processes and technologies, Woodhead Publishing Ltd, Cambridge, UK, pp. 221-257, 2011.
Köpke, PNAS USA, 107: 13087-13092, 2010.
Leang, Appl Environ Microbial, 79: 1102-1109, 2013.
Merkel, FEMS Microbiol Lett, 143: 247-252, 1996.
Mermelstein, Nature Biotechnol, 10: 190-195, 1992.
Murray, Microbial Malec Biol Rev, 64: 412-434, 2000.
Perez, Biotechnol Bioeng, 1-30, 2012.
Phillips, Appl Biochem Biotech, 39: 559-571, 1993.
Rodinov, J Biol Chem, 277: 48949-46959, 2002.
Rubio, J Bacterial, 184: 2827-2832, 2002.
Strätz, Appl Environ Microbiol, 60: 1033-1037, 1994.
Tanner, Int J System Bacterial, 43: 232-236, 1993.
Tirado-Acevedo, Production of bioethanol from synthesis gas using Clostridium ljungdahlii, PhD thesis, North Carolina State University, 2010.

(Continued)

*Primary Examiner* — Robert B Mondesi
*Assistant Examiner* — Todd M Epstein
(74) *Attorney, Agent, or Firm* — Andrea Schoen

(57) ABSTRACT

One or more genes in a biosynthesis pathway for a vitamin or other essential nutrient which is needed for the survival of a microorganism can be used as an effective selective marker to identify cells transformed with an exogenous nucleic acid. The microorganism does not naturally contain or express the one or more gene. This permits genetic manipulations to be performed. It permits lower cost fermentations to be performed. It permits production of the essential nutrient for subsequent commodity use.

8 Claims, 5 Drawing Sheets

Specification includes a Sequence Listing.

(56) References Cited

OTHER PUBLICATIONS

Tracy, Curr Opin Biotechnol, 23: 364-381, 2012.
Tyurin, Appl Environ Microbial, 70: 883-890, 2004.
Tyurin, J Biotech Res, 4: 1-12, 2012.
UniProt, Accession No. A6LWN4, 2011.
UniProt, Accession No. A6LWN5, 2011.
UniProt, Accession No. A6LWN6, 2011.
Williams, J Gen Microbial, 136: 819-826, 1990.
Wolin, J Biol Chem, 238: 2882-2886, 1963.
Kong, AfTHIC, a gene involved in thiamine biosynthesis in *Arabidopsis thaliana*, Cell Research, 18: 566-576, 2008.
Chinese Patent Application No. 2013800393165, Chinese Patent Office, Office Action dated Sep. 5, 2016.

\* cited by examiner

SEQUENCE LISTING

<160> NUMBER OF SEQ ID NOS: 19

<210> SEQ ID NO 1
<211> LENGTH: 3063
<212> TYPE: DNA

<213> ORGANISM: Clostridium ragsdalei

<400> SEQUENCE: 1

```
gcatcctgca ggtaaatttt gttcttcatt aaaaatttag caaaattcct ctaaacttaa      60
atattctaaa gtagtagcac ctatttcttt tcttatttcc tctatacttt tacaagctgc     120
tataagttcc ttttttattc ctatatcaat acctagatga cagcagtatt ttatagaagg     180
tgatgcaatt ctaaaatgaa cttcttttgc tccattttttt aataaagatt taacaacttt     240
tctacaacta gttcctctaa ctatagaatc atctataact attacccttc tcccttttat     300
ttcattaaac aaaggactta actttatgtc taccatactt tctcttagat ttttatgcgg     360
aaatataaaa cttcttactg catatttatt ttttataaaa cctagcccat aaggaattcc     420
agaagccttt gaataaccta tagctgcagg tataccagaa tccggtacac caataactat     480
atccccttca acagcatgat ttttatataa cttttttccc gcactaattc tagattcata     540
cacacttatt ccatctataa tactgtctcc tctagcaaaa tatatatatt caaatgaaca     600
aaatccataa ttttttctta aaacattaa cactttccat tgatttatta cttataataa     660
tcatttctcc aggattaaca tctcttataa attctatttt cagagaagat aatgcacaac     720
tttctgaact tataacataa ttgccatttta attttcctat gcataatggt cttatgccta     780
aagaatctct tactgctatt aatgtatctt tagtagaaag aattagagaa taggaacctt     840
ttaaatattt aagtccatta ataaacttgt cttttatttc tacatgaggt tccatttcca     900
aaagctttaa aattacttct gaatctgaag tagttttaaa aacagcacct ttggctttta     960
attttctttt aagcccctct gcattagtta tatttccatt atgtgcaata gcaatttttcc    1020
ctttaagctc ttgtaatttc tccacatcaa atacctgaga aactaatccc atacctttat    1080
agcagttaat ctgttctcca tctgaaattg ctattcctgc actttcctgt cctctatgtt    1140
gaagagccga aaggccataa tacatgatat tacctaagta aatatcttca ttggaaaata    1200
cgccaaaaat tccacaagcc tctttcggct tatcttcttg aattccttta agctcataca    1260
tcaatcatca tctcttaaaa catttaaatt ttttccttcc ataaccttat tcatatttct    1320
aacagcacac attttttccac acatagtaca tgtatgttca tcttctggtt ttgattcttc    1380
tctatatctt cttgcctttt ctggatctat agataaatca atatttttt tccaattaag    1440
ctctcttcta gctttactca tagcattatc ccagtctctt gcaccttta ttccctttgc    1500
aatatctcct gcatgagctg caattttagt agctatgatt ccttctttca tatcttctaa    1560
gtttggaagt cttaaatgtt ctgctggagt tacataacat agaaaatctg ctcctgaaga    1620
tgcagctatt gctcctccta tagctgatgt aatgtgatca taacctggtg ctatgtctgt    1680
aactaaaggt cctaacacat aaaatggtgc attatgacac aatttctttt ctatctgcat    1740
atttgctttt atttcatcta aactcatatg ccctggtcct tctatcataa cttgtacatt    1800
tctcttccaa gctcttttttg caagctctcc taaagtcata agctccttaa tttgtgaagc    1860
atctgtagaa tcctttatag cacctggtct gcaagcatct cctaaactta tagttacatc    1920
atatttttca catatatcta aaaccttatc aaaatgctcg taaaaaggat tttctttttcc    1980
atttaattcc atccatgcat atattaaagc tccacctctg gatacaatat tcataagtct    2040
ttcatttctc ttaaaaattg ctgcagtctc tctatttata cctgcatgaa tagtcataaa    2100
atccacacca ttttgcgcat gttttttcgat tacacctaaa agttcttctt cagttatgtc    2160
ttttaattct ttgtcataaa atcccactgc atcatacata ggcactgttc ctatcatagc    2220
aggtgacatt tctactagtt tagttctaaa ttcttcagtt tttccaaagc aacttaaatc    2280
```

```
cattatagct tctgctttca tttctaaagc tgtcttaacc ttttctagtt cgtcctctat    2340
gcaattgcag tcctttgaaa ttcccaagtt tacatttatc ttagttttaa ggtattgtcc    2400
cacaccttct ggatctaatg atttatgatt tttattagct ggtattacaa ctgcaccctg    2460
tgcaactaat tccattagtt gtagtggttt catattttct ttagcagcta cccttcccat    2520
ttcctttgta attatgcctt ttttagcaac atccatttgt gtcgtgtaat tcattttaaa    2580
catctcccct aacatatttt tcaaaaacta tgttaaataa aaaaggaggt gattctaaat    2640
ctccctcata ttcatcttta tataaataaa aaaatgcaac cttataaagt tgcattttaa    2700
aactatataa agctcttccc tacgctggaa ttatccagat caggtatgag ggtcagaact    2760
aacagttcta tctcagccta aacatagac cccctagat tatttaattt tacatgtaaa    2820
```

```
ttatatcata tatgtttaat tttttaaact gtacatttt taccttcaa taagtaattg    2880 gagatttaca cccaaatacc cctttaactt cttataataa agttataata taattataag    2940
gtttataaaa agatccagat ttatatacat taacatttta attaaaaatt gataatgttg    3000
aattaattat attttataaa tctaggaaac ctaaagaaag gagataatcg tattgggccc    3060
tgc                                                                   3063
```

<210> SEQ ID NO 2
<211> LENGTH: 1296
<212> TYPE: DNA
<213> ORGANISM: Clostridium ragsdalei

<400> SEQUENCE: 2

```
atggatgttg ctaaaaaagg cataattaca aaggaaatgg gaagggtagc tgctaaagaa      60
aatatgaaac cactacaact aatgaattaa gttgcacagg gtgcagttgt aataccagct    120
aataaaaatc ataaatcatt agatccagaa ggtgtgggac aataccttaa aactaagata    180
aatgtaaact tgggaatttc aaaggactgc aattgcatag aggacgaact agaaaaggtt    240
aagacagctt tagaaatgaa agcagaagct ataatggatt taagttgctt tggaaaaact    300
gaagaattta gaactaaact agtagaaatg tcacctgcta tgataggaac agtgcctatg    360
tatgatgcag tgggatttta tgacaaagaa ttaaaagaca taactgaaga gaacttttta    420
ggtgtaatcg aaaaacatgc gcaaaatggt gtggatttta tgactattca tgcaggtata    480
aatagagaga ctgcagcaat ttttaagaga atgaaagac ttatgaatat tgtatccaga    540
ggtggagctt aatatatgc atggatggaa ttaaatggaa agaaaatcc ttttacgag    600 catttttgata aggttttaga tatatgtgaa aaatatgatg taactataag tttaggagat    660
gcttgcagac caggtgctat aaaggattct acagatgctt cacaaattaa ggagcttatg    720
actttaggag agcttgcaaa aagagcttgg aagagaaatg tacaagttat gatagaagga    780
ccagggcata tgagtttaga tgaaataaaa gcaaatatgc agatagaaaa gaaattgtgt    840
cataatgcac cattttatgt gttaggacct ttagttacag acatagcacc aggttatgat    900
cacattacat cagctatagg aggagcaata gctgcatctt caggagcaga ttttctatgt    960
tatgtaactc cagcagaaca tttaagactt ccaaacttag aagatatgaa agaaggaatc    1020
atagctacta aaattgcagc tcatgcagga gatattgcaa agggaataaa aggtgcaaga    1080
gactgggata tgctatgag taaagctaga agagagctta ttggaaaaaa atatttgat    1140 ttatctatag atccagaaaa ggcaagaaga tatagagaag aatcaaaacc agaagatgaa    1200
catacatgta ctatgtgtgg aaaaatgtgt gctgttagaa atatgaataa ggttatggaa    1260
```

```
ggaaaaaatt taaatgtttt aagagatgat gattga                           1296
```

<210> SEQ ID NO 3
<211> LENGTH: 431
<212> TYPE: PRT
<213> ORGANISM: Clostridium ragsdalei

<400> SEQUENCE: 3

```
Met Asp Val Ala Lys Lys Gly Ile Ile Thr Lys Glu Met Gly Arg Val
1               5                   10                  15

Ala Ala Lys Glu Asn Met Lys Pro Leu Gln Leu Met Glu Leu Val Ala
            20                  25                  30

Gln Gly Ala Val Val Ile Pro Ala Asn Lys Asn His Lys Ser Leu Asp
        35                  40                  45

Pro Glu Gly Val Gly Gln Tyr Leu Lys Thr Lys Ile Asn Val Asn Leu
    50                  55                  60

Gly Ile Ser Lys Asp Cys Asn Cys Ile Glu Asp Glu Leu Glu Lys Val
65                  70                  75                  80

Lys Thr Ala Leu Glu Met Lys Ala Glu Ala Ile Met Asp Leu Ser Cys
                85                  90                  95

Phe Gly Lys Thr Glu Glu Phe Arg Thr Lys Leu Val Glu Met Ser Pro
            100                 105                 110

Ala Met Ile Gly Thr Val Pro Met Tyr Asp Ala Val Gly Phe Tyr Asp
        115                 120                 125

Lys Glu Leu Lys Asp Ile Thr Glu Glu Leu Leu Gly Val Ile Glu
    130                 135                 140

Lys His Ala Gln Asn Gly Val Asp Phe Met Thr Ile His Ala Gly Ile
145                 150                 155                 160

Asn Arg Glu Thr Ala Ala Ile Phe Lys Arg Asn Glu Arg Leu Met Asn
                165                 170                 175

Ile Val Ser Arg Gly Gly Ala Leu Ile Tyr Ala Trp Met Glu Leu Asn
            180                 185                 190

Gly Lys Glu Asn Pro Phe Tyr Glu His Phe Asp Lys Val Leu Asp Ile
        195                 200                 205

Cys Glu Lys Tyr Asp Val Thr Ile Ser Leu Gly Asp Ala Cys Arg Pro
    210                 215                 220

Gly Ala Ile Lys Asp Ser Thr Asp Ala Ser Gln Ile Lys Glu Leu Met
225                 230                 235                 240

Thr Leu Gly Glu Leu Ala Lys Arg Ala Trp Lys Arg Asn Val Gln Val
                245                 250                 255

Met Ile Glu Gly Pro Gly His Met Ser Leu Asp Glu Ile Lys Ala Asn
            260                 265                 270

Met Gln Ile Glu Lys Lys Leu Cys His Asn Ala Pro Phe Tyr Val Leu
        275                 280                 285

Gly Pro Leu Val Thr Asp Ile Ala Pro Gly Tyr Asp His Ile Thr Ser
    290                 295                 300

Ala Ile Gly Gly Ala Ile Ala Ala Ser Ser Gly Ala Asp Phe Leu Cys
305                 310                 315                 320

Tyr Val Thr Pro Ala Glu His Leu Arg Leu Pro Asn Leu Glu Asp Met
                325                 330                 335

Lys Glu Gly Ile Ile Ala Thr Lys Ile Ala Ala His Ala Gly Asp Ile
            340                 345                 350

Ala Lys Gly Ile Lys Gly Ala Arg Asp Trp Asp Asn Ala Met Ser Lys
        355                 360                 365
```

```
Ala Arg Arg Glu Leu Asn Trp Lys Lys Ile Phe Asp Leu Ser Ile Asp
    370                 375                 380

Pro Glu Lys Ala Arg Arg Tyr Arg Glu Glu Ser Lys Pro Glu Asp Glu
385                 390                 395                 400

His Thr Cys Thr Met Cys Gly Lys Met Cys Ala Val Arg Asn Met Asn
                405                 410                 415

Lys Val Met Glu Gly Lys Asn Leu Asn Val Leu Arg Asp Asp Asp
            420                 425                 430
```

<210> SEQ ID NO 4
<211> LENGTH: 672
<212> TYPE: DNA
<213> ORGANISM: Clostridium ragsdalei

<400> SEQUENCE: 4

```
atgtatgagc ttaaaggaat tcaagaagat aagccgaaag aggcttgtgg aatttttggc     60
gtattttcca atgaagatat ttacttaggt aatatcatgt attatggcct ttcggctctt    120
caacatagag gacaggaaag tgcaggaata gcaatttcag atggagaaca gattaactgc    180
tataaaggta tgggattagt ttctcaggta tttgatgtgg agaaattaca agagcttaaa    240
gggaaaattg ctattgcaca taatggaaat ataactaatg cagaggggct taaagaaaaa    300
ttaaaagcca aaggtgctgt ttttaaaact acttcagatt cagaagtaat tttaaagctt    360
ttggaaatgg aacctcatgt agaaataaaa gacaagttta ttaatggact taaatattta    420
aaaggttcct attctctaat tctttctact aaagatacat taatagcagt aagagattct    480
ttaggcataa gaccattatg cataggaaaa ttaaatggca attatgttat aagttcagaa    540
agttgtgcat tatcttctct gaaaatagaa tttataagag atgttaatcc tggagaaatg    600
attattataa gtaataaatc aatggaaagt gttaatgttt ttaagaaaaa attatggatt    660
ttgttcattt ga                                                        672
```

<210> SEQ ID NO 5
<211> LENGTH: 223
<212> TYPE: PRT
<213> ORGANISM: Clostridium ragsdalei

<400> SEQUENCE: 5

```
Met Tyr Glu Leu Lys Gly Ile Gln Glu Asp Lys Pro Lys Glu Ala Cys
1               5                   10                  15

Gly Ile Phe Gly Val Phe Ser Asn Glu Asp Ile Tyr Leu Gly Asn Ile
            20                  25                  30

Met Tyr Tyr Gly Leu Ser Ala Leu Gln His Arg Gly Gln Glu Ser Ala
        35                  40                  45

Gly Ile Ala Ile Ser Asp Gly Glu Gln Ile Asn Cys Tyr Lys Gly Met
    50                  55                  60

Gly Leu Val Ser Gln Val Phe Asp Val Glu Lys Leu Gln Glu Leu Lys
65                  70                  75                  80

Gly Lys Ile Ala Ile Ala His Asn Gly Asn Ile Thr Asn Ala Glu Gly
                85                  90                  95

Leu Lys Glu Lys Leu Lys Ala Lys Gly Ala Val Phe Lys Thr Thr Ser
            100                 105                 110

Asp Ser Glu Val Ile Leu Lys Leu Leu Glu Met Glu Pro His Val Glu
        115                 120                 125

Ile Lys Asp Lys Phe Ile Asn Gly Leu Lys Tyr Leu Lys Gly Ser Tyr
    130                 135                 140
```

```
Ser Leu Ile Leu Ser Thr Lys Asp Thr Leu Ile Ala Val Arg Asp Ser
145                 150                 155                 160

Leu Gly Ile Arg Pro Leu Cys Ile Gly Lys Leu Asn Gly Asn Tyr Val
                165                 170                 175

Ile Ser Ser Glu Ser Cys Ala Leu Ser Ser Leu Lys Ile Glu Phe Ile
            180                 185                 190

Arg Asp Val Asn Pro Gly Glu Met Ile Ile Ile Ser Asn Lys Ser Met
        195                 200                 205

Glu Ser Val Asn Val Phe Lys Lys Lys Leu Trp Ile Leu Phe Ile
    210                 215                 220

<210> SEQ ID NO 6
<211> LENGTH: 507
<212> TYPE: DNA
<213> ORGANISM: Clostridium ragsdalei

<400> SEQUENCE: 6
gtgtatgaat ctagaattag tgcgggaaaa aagttatata aaaatcatgc tgttgaaggg      60
gatatagtta ttggtgtacc ggattctggt atacctgcag ctataggtta ttcaaaggct     120
tctggaattc cttatgggct aggttttata aaaaataaat atgcagtaag aagttttata     180
tttccgcata aaaatctaag agaaagtatg gtagacataa agttaagtcc tttgtttaat     240
gaaataaaag ggagaagggt aatagttata gatgattcta tagttagagg aactagttgt     300
agaaaagttg ttaaatcttt attaaaaaat ggagcaaaag aagttcattt tagaattgca     360
tcaccttcta taaaatactg ctgtcatcta ggtattgata taggaataaa aaaggaactt     420
atagcagctt gtaaaagtat agaggaaata agaaaagaaa taggtgctac tactttagaa     480
tatttaagtt tagaggaatt ttgctaa                                         507

<210> SEQ ID NO 7
<211> LENGTH: 168
<212> TYPE: PRT
<213> ORGANISM: Clostridium ragsdalei

<400> SEQUENCE: 7

Met Tyr Glu Ser Arg Ile Ser Ala Gly Lys Lys Leu Tyr Lys Asn His
1               5                   10                  15

Ala Val Glu Gly Asp Ile Val Ile Gly Val Pro Asp Ser Gly Ile Pro
            20                  25                  30

Ala Ala Ile Gly Tyr Ser Lys Ala Ser Gly Ile Pro Tyr Gly Leu Gly
        35                  40                  45

Phe Ile Lys Asn Lys Tyr Ala Val Arg Ser Phe Ile Phe Pro His Lys
    50                  55                  60

Asn Leu Arg Glu Ser Met Val Asp Ile Lys Leu Ser Pro Leu Phe Asn
65                  70                  75                  80

Glu Ile Lys Gly Arg Arg Val Ile Val Ile Asp Asp Ser Ile Val Arg
                85                  90                  95

Gly Thr Ser Cys Arg Lys Val Val Lys Ser Leu Leu Lys Asn Gly Ala
            100                 105                 110

Lys Glu Val His Phe Arg Ile Ala Ser Pro Ser Ile Lys Tyr Cys Cys
        115                 120                 125

His Leu Gly Ile Asp Ile Gly Ile Lys Lys Glu Leu Ile Ala Ala Cys
    130                 135                 140

Lys Ser Ile Glu Glu Ile Arg Lys Glu Ile Gly Ala Thr Thr Leu Glu
145                 150                 155                 160
```

Tyr Leu Ser Leu Glu Glu Phe Cys
            165

<210> SEQ ID NO 8
<211> LENGTH: 28
<212> TYPE: DNA
<213> ORGANISM: Artificial Sequence
<220> FEATURE:
<223> OTHER INFORMATION: synthetic oligonucleotides ThiC-Apa-F

<400> SEQUENCE: 8
gcagggccca atacgattat ctcctttc                                        28

<210> SEQ ID NO 9
<211> LENGTH: 30
<212> TYPE: DNA
<213> ORGANISM: Artificial Sequence
<220> FEATURE:
<223> OTHER INFORMATION: synthetic oligonucleotides ThiC+PurF-Rev-SbfI

<400> SEQUENCE: 9
gcatcctgca ggtaaatttt gttcttcatt                                      30

<210> SEQ ID NO 10
<211> LENGTH: 3540
<212> TYPE: DNA
<213> ORGANISM: Artificial Sequence
<220> FEATURE:
<223> OTHER INFORMATION: Shuttle vecotor pMTL85246

<400> SEQUENCE: 10
aaactccttt ttgataatct catgaccaaa atcccttaac gtgagttttc gttccactga     60
gcgtcagacc ccgtagaaaa gatcaaagga tcttcttgag atcctttttt tctgcgcgta    120
atctgctgct tgcaaacaaa aaaaccaccg ctaccagcgg tggtttgttt gccggatcaa    180
gagctaccaa ctctttttcc gaaggtaact ggcttcagca gagcgcagat accaaatact    240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccggta    540
agcggcaggg tcggaacagg agagcgcacg agggagcttc caggggggaaa cgcctggtat    600 ctttatagtc ctgtcgggtt tcgccacctc tgacttgagc gtcgattttt gtgatgctcg    660 tcagggggc ggagcctatg gaaaaacgcc agcaacgcgg ccttttttacg gttcctggcc    720 ttttgctggc cttttgctca catgttcttt cctgcgttat cccctgattc tgtggataac    780
cgtattaccg cctttgagtg agctgatacc gctcgccgca gccgaacgac cgagcgcagc    840
gagtcagtga gcgaggaagc ggaagagcgc ccaatacgca gggcccctg caggataaaa    900 aaattgtaga taaattttat aaaatagttt tatctacaat ttttttatca ggaaacagct    960
atgaccgcgg ccgcaaaata gttgataata atgcagagtt ataaacaaag gtgaaaagca   1020
ttacttgtat tcttttttat atattattat aaattaaaat gaagctgtat tagaaaaaat   1080
acacacctgt aatataaaat tttaaattaa tttttaattt tttcaaaatg tattttacat   1140
gtttagaatt ttgatgtata ttaaaatagt agaatacata agatacttaa tttaattaaa   1200
gatagttaag tacttttcaa tgtgcttttt tagatgttta atacaaatct ttaattgtaa   1260

```
aagaaatgct gtactattta ctgtactagt gacgggatta aactgtatta attataaata   1320
aaaaataagt acagttgttt aaaattatat tttgtattaa atctaatagt acgatgtaag   1380
ttattttata ctattgctag tttaataaaa agatttaatt atatacttga aaaggagagg   1440
aatccatatg accatgatta cgaattcgag ctcggtaccc ggggatcctc tagagtcgac   1500
gtcacgcgtc catggagatc tcgaggcctg cagacatgca agcttggcac tggccgtcgt   1560
tttacaacgt cgtgactggg aaaaccctgg cgttacccaa cttaatcgcc ttgcagcaca   1620
tccccctttc gccagctggc gtaatagcga agaggcccgc accgatcgcc cttcccaaca   1680
gttgcgcagc ctgaatggcg aatgcgcta gcataaaaat aagaagcctg catttgcagg   1740
cttcttattt ttatggcgcg ccgcattcac ttcttttcta tataaatatg agcgaagcga   1800
ataagcgtcg gaaagcagc aaaaagtttc cttttgctg ttggagcatg ggggttcagg   1860
gggtgcagta tctgacgtca atgccgagcg aaagcgagcc gaagggtagc atttacgtta   1920
gataaccccc tgtatgctc cgacgcttta tatagaaaag aagattcaac taggtaaaat   1980
cttaatatag gttgagatga taaggtttat aaggaatttg tttgttctaa tttttcactc   2040 atttttgttct aatttctttt aacaaatgtt cttttttttt tagaacagtt atgatatagt   2100
tagaatagtt taaaataagg agtgagaaaa agatgaaaga aagatatgga acagtctata   2160
aaggctctca gaggctcata gacgaagaaa gtggagaagt catagaggta gacaagttat   2220
accgtaaaca aacgtctggt aacttcgtaa aggcatatat agtgcaatta ataagtatgt   2280
tagatatgat tggcggaaaa aaacttaaaa tcgttaacta tatcctagat aatgtccact   2340
taagtaacaa tacaatgata gctacaacaa gagaaatagc aaaagctaca ggaacaagtc   2400
tacaaacagt aataacaaca cttaaaatct tagaagaagg aaatattata aaaagaaaaa   2460
ctggagtatt aatgttaaac cctgaactac taatgagagg cgacgaccaa aaacaaaaat   2520
acctcttact cgaatttggg aactttgagc aagaggcaaa tgaaatagat tgacctccca   2580
ataacaccac gtagttattg ggaggtcaat ctatgaaatg cgattaaggg ccggccgaag   2640
caaacttaag agtgtgttga tagtgcagta tcttaaaatt ttgtataata ggaattgaag   2700
ttaaattaga tgctaaaaat ttgtaattaa gaaggagtga ttcatgaac aaaaatataa   2760 aatattctca aacttttta acgagtgaaa aagtactcaa ccaaataata aaacaattga   2820
atttaaaaga aaccgatacc gtttacgaaa ttggaacagg taaagggcat ttaacgacga   2880
aactggctaa aataagtaaa caggtaacgt ctattgaatt agacagtcat ctattcaact   2940
tatcgtcaga aaaattaaaa ctgaatactc gtgtcacttt aattcaccaa gatattctac   3000
agtttcaatt ccctaacaaa cagaggtata aaattgttgg gagtattcct taccatttaa   3060
gcacacaaat tattaaaaaa gtggttttg aaagccatgc gtctgacatc tatctgattg   3120
ttgaagaagg attctacaag cgtaccttgg atattcaccg aacactaggg ttgctcttgc   3180
acactcaagt ctcgattcag caattgctta agctgccagc ggaatgcttt catcctaaac   3240
caaaagtaaa cagtgtctta ataaaactta cccgccatac cacagatgtt ccagataaat   3300
attggaagct atatacgtac tttgtttcaa aatgggtcaa tcgagaatat cgtcaactgt   3360
ttactaaaaa tcagtttcat caagcaatga aacacgccaa agtaaacaat ttaagtaccg   3420
ttacttatga gcaagtattg tctattttta atagttatct attatttaac gggaggaaat   3480
aattctatga gtcgcttttg taaatttgga aagttacacg ttactaaagg gaatgtgttt   3540
```

<210> SEQ ID NO 11
<211> LENGTH: 6582

<212> TYPE: DNA
<213> ORGANISM: Artificial Sequence
<220> FEATURE:
<223> OTHER INFORMATION: plasmid pMTL85246-thiC-purF

<400> SEQUENCE: 11

| | | | | | |
|---|---|---|---|---|---|
| ggtaaatttt | gttcttcatt | aaaaatttag | caaaattcct | ctaaacttaa | atattctaaa | 60 |
| gtagtagcac | ctatttcttt | tcttatttcc | tctatacttt | tacaagctgc | tataagttcc | 120 |
| tttttattc | ctatatcaat | acctagatga | cagcagtatt | ttatagaagg | tgatgcaatt | 180 |
| ctaaaatgaa | cttcttttgc | tccattttt | aataaagatt | taacaacttt | tctacaacta | 240 |
| gttcctctaa | ctatagaatc | atctataact | attacccttc | tccctttat | ttcattaaac | 300 |
| aaaggactta | actttatgtc | taccatactt | tctcttagat | ttttatgcgg | aaatataaaa | 360 |
| cttcttactg | catatttatt | ttttataaaa | cctagcccat | aaggaattcc | agaagccttt | 420 |
| gaataaccta | tagctgcagg | tataccagaa | tccggtacac | caataactat | atccccttca | 480 |
| acagcatgat | ttttatataa | cttttttccc | gcactaattc | tagattcata | cacacttatt | 540 |
| ccatctataa | tactgtctcc | tctagcaaaa | tatatatatt | caaatgaaca | aaatccataa | 600 |
| tttttttctta | aaaacattaa | cactttccat | tgatttatta | cttataataa | tcatttctcc | 660 |
| aggattaaca | tctcttataa | attctattt | cagagaagat | aatgcacaac | tttctgaact | 720 |
| tataacataa | ttgccatta | attttcctat | gcataatggt | cttatgccta | agaatctct | 780 |
| tactgctatt | aatgtatctt | tagtagaaag | aattagagaa | taggaacctt | ttaaatattt | 840 |
| aagtccatta | ataaacttgt | cttttatttc | tacatgaggt | tccatttcca | aaagctttaa | 900 |
| aattacttct | gaatctgaag | tagttttaaa | aacagcacct | ttggctttta | atttttcttt | 960 |
| aagcccctct | gcattagtta | tatttccatt | atgtgcaata | gcaatttcc | ctttaagctc | 1020 |
| ttgtaatttc | tccacatcaa | atacctgaga | aactaatccc | ataccttat | agcagttaat | 1080 |
| ctgttctcca | tctgaaattg | ctattcctgc | actttcctgt | cctctatgtt | gaagagccga | 1140 |
| aaggccataa | tacatgatat | tacctaagta | aatatcttca | ttggaaaata | cgccaaaaat | 1200 |
| tccacaagcc | tctttcggct | tatcttcttg | aattcctta | agctcataca | tcaatcatca | 1260 |
| tctcttaaaa | catttaaatt | ttttccttcc | ataaccttat | tcatatttct | aacagcacac | 1320 |
| attttttccac | acatagtaca | tgtatgttca | tcttctggtt | ttgattcttc | tctatatctt | 1380 |
| cttgcctttt | ctggatctat | agataaatca | atatttttt | tccaattaag | ctctcttcta | 1440 |
| gctttactca | tagcattatc | ccagtctctt | gcacctttta | ttccctttgc | aatatctcct | 1500 |
| gcatgagctg | caatttttagt | agctatgatt | ccttcttttca | tatcttctaa | gtttggaagt | 1560 |
| cttaaatgtt | ctgctggagt | tacataacat | agaaaatctg | ctcctgaaga | tgcagctatt | 1620 |
| gctcctccta | tagctgatgt | aatgtgatca | taacctggtg | ctatgtctgt | aactaaaggt | 1680 |
| cctaacacat | aaaatggtgc | attatgacac | aatttctttt | ctatctgcat | atttgctttt | 1740 |
| atttcatcta | aactcatatg | ccctggtcct | tctatcataa | cttgtacatt | tctcttccaa | 1800 |
| gctcttttg | caagctctcc | taaagtcata | agctccttaa | tttgtgaagc | atctgtagaa | 1860 |
| tcctttatag | cacctggtct | gcaagcatct | cctaaactta | tagttacatc | atatttttca | 1920 |
| catatatcta | aaaccttatc | aaaatgctcg | taaaaggat | tttcttttcc | atttaattcc | 1980 |
| atccatgcat | atattaaagc | tccacctctg | gatacaatat | tcataagtct | ttcatttctc | 2040 |
| ttaaaaattg | ctgcagtctc | tctatttata | cctgcatgaa | tagtcataaa | atccacacca | 2100 |
| ttttgcgcat | gttttttcgat | tacacctaaa | agttcttctt | cagttatgtc | ttttaattct | 2160 |

```
ttgtcataaa atcccactgc atcatacata ggcactgttc ctatcatagc aggtgacatt   2220
tctactagtt tagttctaaa ttcttcagtt tttccaaagc aacttaaatc cattatagct   2280
tctgctttca tttctaaagc tgtcttaacc ttttctagtt cgtcctctat gcaattgcag   2340
tcctttgaaa ttcccaagtt tacatttatc ttagttttaa ggtattgtcc cacaccttct   2400
ggatctaatg atttatgatt tttattagct ggtattacaa ctgcaccctg tgcaactaat   2460
tccattagtt gtagtggttt catatttcct ttagcagcta cccttcccat ttcctttgta   2520
attatgcctt ttttagcaac atccatttgt gtcgtgtaat tcattttaaa catctccctt   2580
aacatatttt tcaaaaacta tgttaaataa aaaaggaggt gattctaaat ctccctcata   2640
ttcatcttta tataaataaa aaaatgcaac cttataaagt tgcattttaa aactatataa   2700
agctcttccc tacgctggaa ttatccagat caggtatgag ggtcagaact aacagttcta   2760
tctcagccta taacatagac cccctagat tatttaattt tacatgtaaa ttatatcata   2820
tatgtttaat ttttaaact gtacatttt ataccttcaa taagtaattg gagatttaca   2880
cccaaatacc cctttaactt cttataataa agttataata taattataag gtttataaaa   2940
agatccagat ttatatacat taacatttta attaaaaatt gataatgttg aattaattat   3000
attttataaa tctaggaaac ctaaagaaag gagataatcg tattgggccc tgcgtattgg   3060
gcgctcttcc gcttcctcgc tcactgactc gctgcgctcg tcgttcggc tgcggcgagc   3120
ggtatcagct cactcaaagg cggtaatacg gttatccaca gaatcagggg ataacgcagg   3180
aaagaacatg tgagcaaaag gccagcaaaa ggccaggaac cgtaaaaagg ccgcgttgct   3240
ggcgtttttc cataggctcc gcccccctga cgagcatcac aaaaatcgac gctcaagtca   3300
gaggtggcga aacccgacag gactataaag ataccaggcg tttccccctg gaagctccct   3360
cgtgcgctct cctgttccga ccctgccgct taccggatac ctgtccgcct ttctcccttc   3420
gggaagcgtg gcgctttctc atagctcacg ctgtaggtat ctcagttcgg tgtaggtcgt   3480
tcgctccaag ctgggctgtg tgcacgaacc ccccgttcag cccgaccgct gcgccttatc   3540
cggtaactat cgtcttgagt ccaacccggt aagacacgac ttatcgccac tggcagcagc   3600
cactggtaac aggattagca gagcgaggta tgtaggcggt gctacagagt tcttgaagtg   3660
gtggcctaac tacggctaca ctagaagaac agtatttggt atctgcgctc tgctgaagcc   3720
agttaccttc ggaaaaagag ttggtagctc ttgatccggc aaacaaacca ccgctggtag   3780
cggtggtttt tttgtttgca agcagcagat tacgcgcaga aaaaaaggat ctcaagaaga   3840
tcctttgatc ttttctacgg ggtctgacgc tcagtggaac gaaaactcac gttaagggat   3900
tttggtcatg agattatcaa aaaggagttt aaacacattc cctttagtaa cgtgtaactt   3960
tccaaattta caaaagcgac tcatagaatt atttcctccc gttaaataat agataactat   4020
taaaaataga caatacttgc tcataagtaa cggtacttaa attgtttact ttggcgtgtt   4080
tcattgcttg atgaaactga tttttagtaa acagttgacg atattctcga ttgacccatt   4140
ttgaaacaaa gtacgtatat agcttccaat atttatctgg aacatctgtg gtatggcggg   4200
taagttttat taagacactg tttactttg gtttaggatg aaagcattcc gctggcagct   4260
taagcaattg ctgaatcgag acttgagtgt gcaagagcaa ccctagtgtt cggtgaatat   4320
ccaaggtacg cttgtagaat ccttcttcaa caatcagata gatgtcagac gcatggcttt   4380
caaaaaccac ttttttaata atttgtgtgc ttaaatggta aggaatactc ccaacaattt   4440
tatacctctg tttgttaggg aattgaaact gtagaatatc ttggtgaatt aaagtgacac   4500
gagtattcag ttttaatttt tctgacgata agttgaatag atgactgtct aattcaatag   4560
```

-continued

```
acgttacctg tttacttatt ttagccagtt tcgtcgttaa atgcccttta cctgttccaa   4620
tttcgtaaac ggtatcggtt tcttttaaat tcaattgttt tattatttgg ttgagtactt   4680
tttcactcgt taaaaagttt tgagaatatt ttatattttt gttcatgtaa tcactccttc   4740
ttaattacaa atttttagca tctaatttaa cttcaattcc tattatacaa aattttaaga   4800
tactgcacta tcaacacact cttaagtttg cttcggccgg cccttaatcg catttcatag   4860
attgacctcc caataactac gtggtgttat tgggaggtca atctatttca tttgcctctt   4920
gctcaaagtt cccaaattcg agtaagaggt atttttgttt ttggtcgtcg cctctcatta   4980
gtagttcagg gtttaacatt aatactccag tttttctttt tataatattt ccttcttcta   5040
agattttaag tgttgttatt actgtttgta gacttgttcc tgtagctttt gctatttctc   5100
ttgttgtagc tatcattgta ttgttactta agtggacatt atctaggata tagttaacga   5160
ttttaagttt ttttccgcca atcatatcta acatacttat taattgcact atatatgcct   5220
ttacgaagtt accagacgtt tgtttacggt ataacttgtc tacctctatg acttctccac   5280
tttcttcgtc tatgagcctc tgagagcctt tatagactgt tccatatctt tctttcatct   5340
ttttctcact ccttatttta aactattcta actatatcat aactgttcta aaaaaaaaag   5400
aacatttgtt aaaagaaatt agaacaaaat gagtgaaaaa ttagaacaaa caaattcctt   5460
ataaacctta tcatctcaac ctatattaag attttaccta gttgaatctt cttttctata   5520
taaagcgtcg gagcatatca gggggttatc taacgtaaat gctacccttc ggctcgcttt   5580
cgctcggcat tgacgtcaga tactgcaccc cctgaacccc catgctccaa cagcaaaaag   5640
gaaacttttt gctgcttttc cgacgcttat tcgcttcgct catatttata tagaaaagaa   5700
gtgaatgcgg cgcgccataa aaataagaag cctgcaaatg caggcttctt atttttatgc   5760
tagcgccatt cgccattcag gctgcgcaac tgttgggaag ggcgatcggt gcgggcctct   5820
tcgctattac gccagctggc gaaaggggga tgtgctgcaa ggcgattaag ttgggtaacg   5880
ccagggtttt cccagtcacg acgttgtaaa acgacggcca gtgccaagct tgcatgtctg   5940
caggcctcga gatctccatg gacgcgtgac gtcgactcta gaggatcccc gggtaccgag   6000
ctcgaattcg taatcatggt catatggatt cctctccttt tcaagtatat aattaaatct   6060
ttttattaaa ctagcaatag tataaaataa cttacatcgt actattagat ttaatacaaa   6120
atataatttt aaacaactgt acttattttt tatttataat taatacagtt taatcccgtc   6180
actagtacag taaatagtac agcatttctt ttacaattaa agatttgtat taaacatcta   6240
aaaaagcaca ttgaaaagta cttaactatc tttaattaaa ttaagtatct tatgtattct   6300
actattttaa tatacatcaa aattctaaac atgtaaaata cattttgaaa aaattaaaaa   6360
ttaatttaaa attttatatt acaggtgtgt atttttttcta atacagcttc attttaattt   6420
ataataatat ataaaaaaga atacaagtaa tgcttttcac ctttgtttat aactctacat   6480
tattatcaac tattttgcgg ccgcggtcat agctgtttcc tgataaaaaa attgtagata   6540
aaactatttt ataaaattta tctacaattt ttttatcctg ca                       6582
```

```

<210> SEQ ID NO 12
<211> LENGTH: 419
<212> TYPE: DNA
<213> ORGANISM: Clostridium autoethanogenum
<220> FEATURE:
<221> NAME/KEY: promoter
<222> LOCATION: (0)...(0)
<223> OTHER INFORMATION: pta-ack
```

```
<400> SEQUENCE: 12
agaaattttc ctttctaaaa tattttattc catgtcaaga actctgttta tttcattaaa    60
gaactataag tacaaagtat aaggcatttg aaaaaatagg ctagtatatt gattgattat   120
ttattttaaa atgcctaagt gaaatatata catattataa caataaaata agtattagtg   180
taggattttt aaatagagta tctattttca gattaaattt ttgattattt gatttacatt   240
atataatatt gagtaaagta ttgactagca aaattttttg atactttaat ttgtgaaatt   300
tcttatcaaa agttatattt tgaataatt tttattgaaa aatacaacta aaaggatta    360 tagtataagt gtgtgtaatt ttgtgttaaa tttaaaggga ggaaatgaac atgaaattg   419

<210> SEQ ID NO 13
<211> LENGTH: 2781
<212> TYPE: DNA
<213> ORGANISM: Artificial Sequence
<220> FEATURE:
<223> OTHER INFORMATION: plasmid pGS20

<400> SEQUENCE: 13
tttgccacct gacgtctaag aaaaggaata ttcagcaatt tgcccgtgcc gaagaaaggc    60
ccacccgtga aggtgagcca gtgagttgat tgctacgtaa ttagttagtt agcccttagt   120
gactcgtaat acgactcact atagggctcg agtctagaga attcgatatc acccgggaac   180
tagtctgcag ccctttagtg agggttaatt ggagtcacta agggttagtt agttagatta   240
gcagaaagtc aaaagcctcc gaccggaggc ttttgactaa aacttcccct ggggttatca   300
ttggggctca ctcaaaggcg gtaatcagat aaaaaaaatc cttagctttc gctaaggatg   360
atttctgcta gagatggaat agactggatg gaggcggata agttgcagg accacttctg    420 cgctcggccc ttccggctgg ctggtttatt gctgataaat ctggagccgg tgagcgtggg   480
tctcgcggta tcattgcagc actggggcca gatggtaagc cctcccgtat cgtagttatc   540
tacacgacgg ggagtcaggc aactatggat gaacgaaata gacagatcgc tgagataggt   600
gcctcactga ttaagcattg gtaactgtca gaccaagttt actcatatat actttagatt   660
gatttaaaac ttcattttta atttaaaagg atctaggtga agatcctttt tgataatctc   720
atgaccaaaa tcccttaacg tgagttttcg ttccactgag cgtcagaccc cttaataaga   780
tgatcttctt gagatcgttt tggtctgcgc gtaatctctt gctctgaaaa cgaaaaaacc   840
gccttgcagg gcggtttttc gaaggttctc tgagctacca actctttgaa ccgaggtaac   900
tggcttggag gagcgcagtc accaaaactt gtccttttcag tttagcctta accggcgcat   960
gacttcaaga ctaactcctc taaatcaatt accagtggct gctgccagtg gtgcttttgc  1020
atgtctttcc gggttggact caagacgata gttaccggat aaggcgcagc ggtcggactg  1080
aacggggggt tcgtgcatac agtccagctt ggagcgaact gcctacccgg aactgagtgt  1140
caggcgtgga atgagacaaa cgcggccata acagcggaat gacaccggta aaccgaaagg  1200
caggaacagg agagcgcacg agggagccgc caggggaaac gcctggtatc tttatagtcc  1260
tgtcgggttt cgccaccact gatttgagcg tcagatttcg tgatgcttgt caggggggcg  1320
gagcctatgg aaaaacggct ttgccgcggc cctctcactt ccctgttaag tatcttcctg  1380
gcatcttcca ggaaatctcc gccccgttcg taagccattt ccgctcgccg cagtcgaacg  1440
accgagcgta gcgagtcagt gagcgaggaa gcggaatata tcctgtatca catattctgc  1500
tgacgcaccg gtgcagcctt ttttctcctg ccacatgaag cacttcactg acaccctcat  1560
cagtgccaac atagtaagcc agtatacact ccgctagcgc tgaggtctgc ctcgtgaaga  1620
```

```
aggtgttgct gactcatacc aggcctgaat cgccccatca tccagccaga aagtgaggga    1680
gccacggttg atgagagctt tgttgtaggt ggaccagttg gtgattttga acttttgctt    1740
tgccacggaa cggtctgcgt tgtcgggaag atgcgtgatc tgatccttca actcagcaaa    1800
agttcgattt attcaacaaa gccacgttgt gtctcaaaat ctctgatgtt acattgcaca    1860
agataaaaat atatcatcat gaacaataaa actgtctgct tacataaaca gtaatacaag    1920
gggtgtttac tagaggttga tcgggcacgt aagaggttcc aactttcacc ataatgaaat    1980
aagatcacta ccgggcgtat tttttgagtt atcgagattt tcaggagcta aggaagctaa    2040
aatggagaaa aaaatcacgg gatataccac cgttgatata tcccaatggc atcgtaaaga    2100
acattttgag gcatttcagt cagttgctca atgtacctat aaccagaccg ttcagctgga    2160
tattacggcc ttttttaaaga ccgtaaagaa aaataagcac aagttttatc ggcctttat    2220 tcacattctt gcccgcctga tgaacgctca cccggagttt cgtatggcca tgaaagacgg    2280
tgagctggtg atctgggata gtgttcaccc ttgttacacc gttttccatg agcaaactga    2340
aacgttttcg tccctctgga gtgaatacca cgacgatttc cggcagtttc tccacatata    2400
ttcgcaagat gtggcgtgtt acggtgaaaa cctggcctat ttccctaaag ggtttattga    2460
gaatatgttt tttgtctcag ccaatccctg ggtgagtttc accagttttg atttaaacgt    2520
ggccaatatg gacaacttct tcgcccccgt tttcacgatg ggcaaatatt atacgcaagg    2580
cgacaaggtg ctgatgccgc tggcgatcca ggttcatcat gccgtttgtg atggcttcca    2640
tgtcggccgc atgcttaatg aattacaaca gtactgtgat gagtggcagg gcggggcgta    2700
ataatactag ctccggcaaa aaaacgggca aggtgtcacc accctgccct ttttctttaa    2760
aaccgaaaag attacttcgc g                                              2781
```

<210> SEQ ID NO 14
<211> LENGTH: 601
<212> TYPE: PRT
<213> ORGANISM: Artificial Sequence
<220> FEATURE:
<223> OTHER INFORMATION: designed methyltransferase
<400> SEQUENCE: 14

```
Met Phe Pro Cys Asn Ala Tyr Ile Glu Tyr Gly Asp Lys Asn Met Asn
1               5                   10                  15

Ser Phe Ile Glu Asp Val Glu Gln Ile Tyr Asn Phe Ile Lys Lys Asn
            20                  25                  30

Ile Asp Val Glu Glu Lys Met His Phe Ile Glu Thr Tyr Lys Gln Lys
        35                  40                  45

Ser Asn Met Lys Lys Glu Ile Ser Phe Ser Glu Glu Tyr Tyr Lys Gln
    50                  55                  60

Lys Ile Met Asn Gly Lys Asn Gly Val Val Tyr Thr Pro Pro Glu Met
65                  70                  75                  80

Ala Ala Phe Met Val Lys Asn Leu Ile Asn Val Asn Asp Val Ile Gly
                85                  90                  95

Asn Pro Phe Ile Lys Ile Ile Asp Pro Ser Cys Gly Ser Gly Asn Leu
            100                 105                 110

Ile Cys Lys Cys Phe Leu Tyr Leu Asn Arg Ile Phe Ile Lys Asn Ile
        115                 120                 125

Glu Val Ile Asn Ser Lys Asn Asn Leu Asn Leu Lys Leu Glu Asp Ile
    130                 135                 140

Ser Tyr His Ile Val Arg Asn Asn Leu Phe Gly Phe Asp Ile Asp Glu
```

-continued

```
            145                 150                 155                 160
        Thr Ala Ile Lys Val Leu Lys Ile Asp Leu Phe Leu Ile Ser Asn Gln
                        165                 170                 175
        Phe Ser Glu Lys Asn Phe Gln Val Lys Asp Phe Leu Val Glu Asn Ile
                        180                 185                 190
        Asp Arg Lys Tyr Asp Val Phe Ile Gly Asn Pro Pro Tyr Ile Gly His
                        195                 200                 205
        Lys Ser Val Asp Ser Ser Tyr Ser Tyr Val Leu Arg Lys Ile Tyr Gly
                210                 215                 220
        Ser Ile Tyr Arg Asp Lys Gly Asp Ile Ser Tyr Cys Phe Phe Gln Lys
        225                 230                 235                 240
        Ser Leu Lys Cys Leu Lys Glu Gly Gly Lys Leu Val Phe Val Thr Ser
                        245                 250                 255
        Arg Tyr Phe Cys Glu Ser Cys Ser Gly Lys Glu Leu Arg Lys Phe Leu
                        260                 265                 270
        Ile Glu Asn Thr Ser Ile Tyr Lys Ile Asp Phe Tyr Gly Ile Arg
                        275                 280                 285
        Pro Phe Lys Arg Val Gly Ile Asp Pro Met Ile Ile Phe Leu Val Arg
                        290                 295                 300
        Thr Lys Asn Trp Asn Asn Asn Ile Glu Ile Ile Arg Pro Asn Lys Ile
        305                 310                 315                 320
        Glu Lys Asn Glu Lys Asn Lys Phe Leu Asp Ser Leu Phe Leu Asp Lys
                        325                 330                 335
        Ser Glu Lys Cys Lys Lys Phe Ser Ile Ser Gln Lys Ser Ile Asn Asn
                        340                 345                 350
        Asp Gly Trp Val Phe Val Asp Glu Val Glu Lys Asn Ile Ile Asp Lys
                        355                 360                 365
        Ile Lys Glu Lys Ser Lys Phe Ile Leu Lys Asp Ile Cys His Ser Cys
                        370                 375                 380
        Gln Gly Ile Ile Thr Gly Cys Asp Arg Ala Phe Ile Val Asp Arg Asp
        385                 390                 395                 400
        Ile Ile Asn Ser Arg Lys Ile Glu Leu Arg Leu Ile Lys Pro Trp Ile
                        405                 410                 415
        Lys Ser Ser His Ile Arg Lys Asn Glu Val Ile Lys Gly Glu Lys Phe
                        420                 425                 430
        Ile Ile Tyr Ser Asn Leu Ile Glu Asn Glu Thr Glu Cys Pro Asn Ala
                        435                 440                 445
        Ile Lys Tyr Ile Glu Gln Tyr Lys Lys Arg Leu Met Glu Arg Arg Glu
                        450                 455                 460
        Cys Lys Lys Gly Thr Arg Lys Trp Tyr Glu Leu Gln Trp Gly Arg Lys
        465                 470                 475                 480
        Pro Glu Ile Phe Glu Glu Lys Lys Ile Val Phe Pro Tyr Lys Ser Cys
                        485                 490                 495
        Asp Asn Arg Phe Ala Leu Asp Lys Gly Ser Tyr Phe Ser Ala Asp Ile
                        500                 505                 510
        Tyr Ser Leu Val Leu Lys Lys Asn Val Pro Phe Thr Tyr Glu Ile Leu
                        515                 520                 525
        Leu Asn Ile Leu Asn Ser Pro Leu Tyr Glu Phe Tyr Phe Lys Thr Phe
                        530                 535                 540
        Ala Lys Lys Leu Gly Glu Asn Leu Tyr Glu Tyr Tyr Pro Asn Asn Leu
        545                 550                 555                 560
        Met Lys Leu Cys Ile Pro Ser Ile Asp Phe Gly Gly Glu Asn Asn Ile
                        565                 570                 575
```

```
Glu Lys Lys Leu Tyr Asp Phe Phe Gly Leu Thr Asp Lys Glu Ile Glu
            580                 585                 590

Ile Val Glu Lys Ile Lys Asp Asn Cys
        595                 600
```

<210> SEQ ID NO 15
<211> LENGTH: 1940
<212> TYPE: DNA
<213> ORGANISM: Artificial Sequence
<220> FEATURE:
<223> OTHER INFORMATION: designed methyltransferase gene fused with an inducible lac promoter

<400> SEQUENCE: 15

| | | | | | |
|---|---|---|---|---|---|
| gcggccgcgc | aacgcaatta | atgtgagtta | gctcactcat | taggcacccc | aggctttaca | 60 |
| ctttatgctt | ccggctcgta | tgttgtgtgg | aattgtgagc | ggataacaat | ttcacacagg | 120 |
| aaacacatat | gtttccgtgc | aatgcctata | tcgaatatgg | tgataaaaat | atgaacagct | 180 |
| ttatcgaaga | tgtggaacag | atctacaact | tcattaaaaa | gaacattgat | gtggaagaaa | 240 |
| agatgcattt | cattgaaacc | tataaacaga | aaagcaacat | gaagaaagag | attagcttta | 300 |
| gcgaagaata | ctataaacag | aagattatga | cggcaaaaa | tggcgttgtg | tacacccgc | 360 |
| cggaaatggc | ggcctttatg | gttaaaaatc | tgatcaacgt | taacgatgtt | attggcaatc | 420 |
| cgtttattaa | aatcattgac | ccgagctgcg | gtagcggcaa | tctgatttgc | aaatgttttc | 480 |
| tgtatctgaa | tcgcatcttt | attaagaaca | ttgaggtgat | taacagcaaa | aataacctga | 540 |
| atctgaaact | ggaagacatc | agctaccaca | tcgttcgcaa | caatctgttt | ggcttcgata | 600 |
| ttgacgaaac | cgcgatcaaa | gtgctgaaaa | ttgatctgtt | tctgatcagc | aaccaattta | 660 |
| gcgagaaaaa | tttccaggtt | aaagactttc | tggtggaaaa | tattgatcgc | aaatatgacg | 720 |
| tgttcattgg | taatccgccg | tatatcggtc | acaaaagcgt | ggacagcagc | tacagctacg | 780 |
| tgctgcgcaa | aatctacggc | agcatctacc | gcgacaaagg | cgatatcagc | tattgtttct | 840 |
| ttcagaagag | cctgaaatgt | ctgaaggaag | gtggcaaact | ggtgtttgtg | accagccgct | 900 |
| acttctgcga | gagctgcagc | ggtaaagaac | tgcgtaaatt | cctgatcgaa | aacacgagca | 960 |
| tttacaagat | cattgatttt | tacggcatcc | gcccgttcaa | acgcgtgggt | atcgatccga | 1020 |
| tgattatttt | tctggttcgt | acgaagaact | ggaacaataa | cattgaaatt | attcgcccga | 1080 |
| acaagattga | aaagaacgaa | aagaacaaat | tcctggatag | cctgttcctg | acaaaaagcg | 1140 |
| aaaagtgtaa | aaagtttagc | attagccaga | aaagcattaa | taacgatggc | tgggttttcg | 1200 |
| tggacgaagt | ggagaaaaac | attatcgaca | aaatcaaaga | gaaaagcaag | ttcattctga | 1260 |
| aagatatttg | ccatagctgt | caaggcatta | tcaccggttg | tgatcgcgcc | tttattgtgg | 1320 |
| accgtgatat | catcaatagc | cgtaagatcg | aactgcgtct | gattaaaccg | tggattaaaa | 1380 |
| gcagccatat | ccgtaagaat | gaagttatta | gggcgaaaa | attcatcatc | tatagcaacc | 1440 |
| tgattgagaa | tgaaaccgag | tgtccgaatg | cgattaaata | tatcgaacag | tacaagaaac | 1500 |
| gtctgatgga | gcgccgcgaa | tgcaaaaagg | gcacgcgtaa | gtggtatgaa | ctgcaatggg | 1560 |
| gccgtaaacc | ggaaatcttc | gaagaaaaga | aaattgtttt | cccgtataaa | agctgtgaca | 1620 |
| atcgttttgc | actggataag | ggtagctatt | ttagcgcaga | catttatagc | ctggttctga | 1680 |
| agaaaaatgt | gccgttcacc | tatgagatcc | tgctgaatat | cctgaatagc | ccgctgtacg | 1740 |
| agttttactt | taagaccttc | gcgaaaaagc | tgggcgagaa | tctgtacgag | tactatccga | 1800 |
| acaacctgat | gaagctgtgc | atcccgagca | tcgatttcgg | cggtgagaac | aatattgaga | 1860 |

```
aaaagctgta tgatttcttt ggtctgacgg ataaagaaat tgagattgtg gagaagatca    1920
aagataactg ctaagaattc                                                1940

<210> SEQ ID NO 16
<211> LENGTH: 51
<212> TYPE: DNA
<213> ORGANISM: Artificial Sequence
<220> FEATURE:
<223> OTHER INFORMATION: oligonucleotide primer

<400> SEQUENCE: 16
aggaaatgaa catgaaacat gtgaaaaata cagtattaac ttttaaacaa g             51

<210> SEQ ID NO 17
<211> LENGTH: 58
<212> TYPE: DNA
<213> ORGANISM: Artificial Sequence
<220> FEATURE:
<223> OTHER INFORMATION: oligonucleotide primer

<400> SEQUENCE: 17
gacgtcgact ctagaggatc ttattcattt gattcataat tagttatttc ttttattg      58

<210> SEQ ID NO 18
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 18
tgtaaaacga cggccagt                                                  18

<210> SEQ ID NO 19
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 19
caggaaacag ctatgacc                                                  18
```

VITAMIN PROTOTROPHY AS A SELECTABLE MARKER

CROSS REFERENCE TO RELATED APPLICATIONS

This application is a continuation of U.S. patent application Ser. No. 13/900,172 filed May 22, 2013, which claims the benefit of U.S. Provisional Patent Application No. 61/650,757 filed on May 23, 2012, which contents are incorporated by reference in their entirety.

FIELD OF THE INVENTION

The invention relates to recombinant microorganisms, methods for the production of one or more products by fermentation, and selection methods.

BACKGROUND OF THE INVENTION

Selectable (or selective) markers and agents are important for genetically modifying cells or microorganisms. They can be used to screen for cells with introduced DNA: A selectable marker protects the organism from the presence or absence of a selective agent that would normally kill it or prevent its growth. Usually antibiotic resistance genes are used as selectable markers, and the respective antibiotic as selective agent.

Use of selectable agents like antibiotics adds significant costs to a process like an industrial fermentation. Some antibiotics are also not or only poorly soluble in water and need to be dissolved in solvents. This adds further costs and potentially has a negative effect on the microbial cells; for example, chloramphenicol and thiamphenicol need to be dissolved in Ethanol or Dimethylformamide (DMF), respectively.

Some organisms are also naturally resistant to some antibiotics and so they can not be used as selectable agents. For example, most antibiotics classes are only active against either Gram-positive or Gram-negative bacteria as they target cell wall compounds and several Genera have natural resistance against specific antibiotics (for example, Clostridia against Chloramphenicol, as they posses chloramphenicol acetyltransferase genes that confer resistance and are also able to reduce the aryl-nitro-residue of the molecule to inactivate it (O'Brien & Morris, 1971, *J Gen Microbiol*, 67: 265-271)).

In addition, some antibiotic substances get inactivated or cannot be used under typical process conditions. For example, the low pH between 4-5.5 used in several fermentation processes inactivates the macrolide erythromycin, while on the other hand it's analogue clarithromycin only dissolves at extremely low pH below 2 (Mermelstein & Papoutsakis, 1993, *FEMS Microbial Lea*, 113: 71-76).

Auxotrophic markers that can compensate for an inability to metabolise certain amino acids, nucleotides, or sugars can also be used for selection. However, these also require the addition of compounds to the media which are not otherwise needed, increasing expense.

Reporter genes have also been used to allow for selection of successful transformants during processes for producing recombinant microorganisms; for example, genes encoding green fluorescent protein or beta-galactosidase (lacZ). However, these can be toxic to the cells and the products produced undesirable in commercial fermentation reactions.

It is an object of the invention to overcome one or more of the disadvantages of the prior art, or to at least to provide the public with a useful choice.

SUMMARY OF THE INVENTION

The invention generally provides, inter alia, methods for the production of one or more products by microbial fermentation of a substrate, genetically modified microorganisms of use in such methods, nucleic acids suitable for preparation of genetically modified microorganisms, and methods for the selection of certain microorganisms in a mixed population of microorganisms or prevention of the growth of undesirable microorganisms.

In a first aspect, the invention provides an recombinant microorganism comprising at least one exogenous nucleic acid adapted to express one or more enzymes in one or more vitamin biosynthesis pathway, such that the recombinant microorganism can produce the one or more vitamin(s), wherein the recombinant microorganism is an anaerobe.

In one embodiment, the at least one exogenous nucleic acid encodes one or more gene encoding one or more enzymes in the one or more vitamin biosynthesis pathway.

In one embodiment, the one or more vitamin is needed for growth of the microorganism. In one embodiment, the one or more vitamin is essential for growth of the microorganism.

In one embodiment, the at least one exogenous nucleic acid comprises one or more gene which is lacking in a parental microorganism from which the recombinant microorganism is derived.

In one embodiment, the invention provides a recombinant microorganism capable of producing one or more enzyme of one or more vitamin biosynthesis pathway, the microorganism comprising one or more exogenous nucleic acid encoding the one or more enzyme, wherein the recombinant microorganism is derived from a parental microorganism that lacks one or more nucleic acid encoding the one or more enzyme.

In one embodiment, the one or more vitamin is chosen from the group comprising thiamine, pathothenate, riboflavin, nicotinic acid, pyridoxine, biotin, folic acid, and cyanocobalamine. In one particular embodiment, the vitamin is thiamine (B1) and/or panthothenate (B5).

In one embodiment, the one or more of the enzymes is chosen from the group herein after described. In one particular embodiment, the one or more enzymes is chosen from thiamine biosynthesis protein ThiC (EC 4.1.99.17), 3-methyl-2-oxobutanoate hydroxymethyltransferase PanB (EC 2.1.2.11), pantoate-beta-alanine ligase PanC (EC 6.3.2.1), and aspartate 1-decarboxylase Pan D (EC 4.1.1.11). In one embodiment, the enzyme is ThiC. In another embodiment, the one or more enzymes are PanB, PanC and PanD, in combination.

In one embodiment, the microorganism is selected from the group comprising In one particular embodiment, the microorganism is selected from the group comprising Genera *Clostridium, Eubacterium, Peptostreptococcus, Peptococcus, Actinomyces, Lactobacillus, Bifidobacterium, Propionibacterium, Bacteroides, Fusobacterium, Campylobacter,* or *Veillonella*.

In one embodiment, the microorganism is a carboxydotrophic acetogenic bacteria.

In one particular embodiment, the microorganism is selected from the group comprising *Clostridium autoethanogenum, Clostridium ljungdahlii, Clostridium ragsdalei, Clostridium carboxidivorans, Clostridium drakei,*

*Clostridium scatologenes, Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii,* and *Thermoanaerobacter kiuvi.*

In one embodiment the microorganism is *Clostridium autoethanogenum* or *Clostridium ljungdahlii*. In one particular embodiment, the microorganism is *Clostridium autoethanogenum* DSM23693. In another particular embodiment, the microorganism is *Clostridium ljungdahlii* DSM13528 (or ATCC55383).

In one particular embodiment, the microorgism is chosen from *Clostridium autoethanogenum* or *Clostridium ljungdahlii*, and the enzyme is ThiC. In another particular embodiment, the microorganism is *Clostridium autoethanogenum, Clostridium ljungdahlii, Clostridium ragsdalei* or *Acetobacterium woodii* and the enzymes are PanB, PanC and PanD.

In one embodiment, the invention comprises a recombinant bacteria that does not require supplementation with any vitamins.

In a second aspect, the invention provides a nucleic acid encoding one or more enzymes in one or more biosynthesis pathway which produces one or more vitamins.

In one embodiment, the nucleic acid encodes two or more enzymes. In one embodiment, the nucleic acids of the invention encode 3, 4, 5 or 6 such enzymes.

In one embodiment, the one or more vitamin is chosen from the group comprising thiamine, pathothenate, riboflavin, nicotinic acid, pyridoxine, biotin, folic acid, and cyanocobalamine. In one particular embodiment, the vitamin is thiamine (B1) or panthothenate (B5).

In one embodiment, the one or more of the enzymes is as herein after described.

In third aspect, the invention provides a nucleic acid construct or vector comprising one or more nucleic acid of the second aspect.

In one particular embodiment, the nucleic acid construct or vector is an expression construct or vector. In one particular embodiment, the expression construct or vector is a plasmid.

In a fourth aspect, the invention provides host organisms comprising any one or more of the nucleic acids of the second aspect or vectors or constructs of the third aspect.

In a fifth aspect, the invention provides a composition comprising an expression construct or vector as referred to in the third aspect of the invention and a methylation construct or vector.

Preferably, the composition is able to produce a recombinant microorganism according to the first aspect of the invention.

In one particular embodiment, the expression construct/vector and/or the methylation construct/vector is a plasmid.

In a sixth aspect, the invention provides a method of producing one or more products by microbial fermentation comprising fermenting a substrate using a recombinant microorganism of the first aspect of the invention.

In one embodiment, the substrate is chosen from a substrate comprising CO, carbon dioxide and hydrogen, glycerol, fatty acids, starch, molasses, pentoses and hexoses sugars, biomass.

In one particular embodiment, the substrate is a substrate comprising CO. In this embodiment, the methods of the invention may be used to reduce the total atmospheric carbon emissions from an industrial process.

Preferably, the fermentation comprises the steps of fermenting a substrate in a bioreactor to produce the one or more products using a recombinant microorganism of the invention.

In one embodiment the method comprises the steps of:
(a) providing a substrate to a bioreactor containing a culture of one or more microorganism of the invention; and
(b) anaerobic fermentation by the culture in the bioreactor to produce the one or more products.

In one embodiment the method comprises the steps of:
(a) capturing CO-containing gas produced as a result of the industrial process, before the gas is released into the atmosphere;
(b) the anaerobic fermentation of the CO-containing gas to produce the one or more products by a culture containing one or more microorganism of the first aspect of the invention.

In particular embodiments of the method aspects, the microorganism is maintained in an aqueous culture medium.

In particular embodiments of the method aspects, the fermentation of the substrate takes place in a bioreactor.

In a particular embodiment, the substrate comprising CO is a gaseous substrate comprising CO. In one embodiment, the substrate comprises an industrial waste gas. In certain embodiments, the gas is steel mill waste gas or syngas.

In one embodiment, the substrate will typically contain a major proportion of CO, such as at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

In certain embodiments the methods further comprise the step of recovering one or more of the one or more products from the fermentation broth.

In certain embodiments, the one or more products include ethanol, acetate, butanol, isopropanol, one or more vitamins, acetone, 2,3-butanediol.

In one particular embodiment, the one or more product is one or more vitamin.

In one embodiment, the one or more product (in one embodiment, a vitamin) is recovered from the fermentation and passed to one or more further bioreactor to support the growth of, or support the fermentation of a substrate by, one or more second microorganism.

In one embodiment, the one or more second microorganism is a microorganism which is unable to produce, or unable to produce at sufficient levels, the one or more product (in one embodiment, a vitamin) and requires its growth or fermentation media to be supplemented with the one or more product (in one embodiment, a vitamin) to ensure or maintain growth or fermentation, or to increase the efficiency of growth or fermentation.

In one embodiment, the methods of the invention may further comprise fermentation of a substrate by the one or more second microorganism to produce one or more products. In one embodiment, the one or more products may then be recovered from the fermentation broth.

In a seventh aspect, the invention provides one or more products produced by the method of the sixth aspect. In certain embodiments, the one or more products include ethanol, acetate, butanol, isopropanol, one or more vitamins, acetone, 2,3-butanediol.

In an eighth aspect, the invention provides a method for the production of a microorganism of the first aspect of the invention comprising transforming a parental microorganism with one or more exogenous nucleic acid which is adapted to express one or more enzyme in one or more vitamin biosynthesis pathway which produces one or more vitamins.

In certain embodiments, the one or more vitamins and enzymes are as herein after described.

In a nineth aspect, the invention provides a method for the selection of microorganism A in a mixed population of microorganisms, wherein microorganism A is a recombinant microorganism comprising at least one exogenous nucleic acid which is adapted to express one or more enzymes in one or more vitamin biosynthesis pathway which produces one or more vitamin(s) which are needed for the growth of the microorganism, such that the microorganism A can produce the one or more vitamin(s), the method comprising subjecting the mixed population of microorganisms to growth conditions including a media which lacks the one or more vitamin(s).

In one embodiment, the one or more vitamin is essential for growth of the microorganism.

In one embodiment, the at least one exogenous nucleic acid encodes one or more gene encoding one or more enzymes in one or more vitamin biosynthesis pathway.

In one embodiment, the one or more vitamin is as herein before described.

In one embodiment, the one or more of the enzyme is as herein after described.

In one embodiment, the media is chosen from any appropriate media suitable for culturing one or more microorganism.

In one embodiment, the method is performed to distinguish between recombinant and non-recombinant microorganisms during the process of producing recombinant microorganisms.

In another embodiment, the method is performed to select against contaminating microorganisms during growth of, and/or fermentation of a substrate by, microorganism A.

In a tenth aspect, the invention provides a means of preventing the growth of one or more undesirable microorganism in a microbial culture or a fermentation broth, wherein the microbial culture or fermentation broth comprises microorganism A and a nutrient media, wherein microorganism A is a recombinant microorganism comprising at least one exogenous nucleic acid which is adapted to express one or more enzymes in one or more vitamin biosynthesis pathway which produces one or more vitamin(s) which is needed for the growth of microorganism A and the undesirable microorganism(s), such that the microorganism A can produce the one or more vitamin(s), wherein the media lacks the one or more vitamin(s) which is needed for the growth of the microorganisms.

In an eleventh aspect, the invention provides a method for the selective growth or culture of a microorganism A, and wherein microorganism A is a recombinant microorganism comprising at least one exogenous nucleic acid which is adapted to express one or more enzymes in one or more vitamin biosynthesis pathway which produces one or more vitamin(s) which are needed for the growth of the microorganism, such that the microorganism A can produce the one or more vitamin(s), and wherein the growth or culture media lacks the one or more vitamin(s).

In one embodiment, the conditions select against the growth of one or more undesirable microorganism(s).

In a twelfth aspect, the invention provides a method for the production of one or more products by microbial fermentation of a substrate by a microorganism A, wherein microorganism A is a recombinant microorganism comprising at least one exogenous nucleic acid which is adapted to express one or more enzymes in one or more vitamin biosynthesis pathway which produces one or more vitamin(s) which are needed for the growth of the microorganism, such that the microorganism A can produce the one or more vitamin(s), and wherein fermentation occurs in or on a growth media which lacks the one or more vitamin(s).

In one embodiment, the conditions select for growth of microorganism A and against the growth of one or more undesirable microorganism(s).

The microorganisms of the nineth, tenth, eleventh and twelfth aspects of the invention may be chosen from any microorganism of interest, and are not limited to anaerobes. However, in one embodiment they are chosen from the group of anaerobic microorganisms. In one embodiment, they are chosen from the group of carboxydotrophic acetogens.

Microbes and Growing them

Isolated, genetically engineered, carboxydotrophic, acetogenic bacteria are contemplated. These may be prototrophic for thiamine, pantothenate, riboflavin, nicotinic acid, pyridoxine, biotin, folic acid, and/or cyanocobalamine by virtue of an exogenous biosynthetic gene in the biosynthetic pathway for the vitamin. For example an exogenous thiC gene and/or an exogenous panBCD gene cluster may be used to convert an auxotroph to a prototroph. In various embodiments the bacteria may be *Clostridium autoethanogenum*, *Clostridium ljungdahlii*, *Clostridium ragsdalei*, *Clostridium carboxidivorans*, *Clostridium drakei*, *Clostridium scatologenes*, *Butyribacterium methylotrophicum*, *Acetobacterium woodii*, *Alkalibaculum bacchii*, *Blautia producta*, *Eubacterium limosum*, *Moorella thermoacetica*, *Moorella thermautotrophica*, *Oxobacter pfennigii*, or *Thermoanaerobacter kiuvi*. In certain embodiments they are *Clostridium* bacteria such as *C. ljundahlii*, *C. autoethanogenum*, *C. ragsdalei*, and *C. carboxidivorans*. Optionally the bacterium is unable to convert 1-(5'-Phosphoribosyl)-5-aminoimidazole ribonucleotide (AIR) to 4-amino-5-hydroxymethyl-2-methylpyrimidine in the absence of said exogenous thiC gene. An exogenous thiC gene from *C. ragsdalei* is contemplated and exemplified below. The exogenous thiC gene can be on a plasmid, such that the bacterium is auxotrophic for thiamine when cured of a plasmid. Alternatively it is contemplated that the bacterium is auxotrophic for pantothenate when cured of a plasmid. In certain embodiments, isolated, generically engineered, carboxydotrophic bacteria are contemplated. In certain embodiments the bacteria maybe *C. beijerinckii*, *C. acetobutylicum*, *C. saccharoperbutylacetonicum*, *C. phytofermentans*, *C. thermocellum*, *C. cellulovorans*, *C. cellulolyticum*.

One particular exogenous panBCD gene cluster which may be used is from *C. beijerenckei*.

The isolated genetically engineered carboxydotrophic acetogenic bacteria may be cultured by growing them in a medium comprising a gaseous carbon source; the carbon source may comprise CO. Similarly, the bacteria may be cultured in a medium comprising an energy source which comprises CO. It is contemplated that the culture may be strictly anaerobic. It is further contemplated that if the bacterium comprises an exogenous thiC gene that the medium can be devoid of thiamine. In some embodiments the bacterium will comprise an exogenous panBCD gene cluster and the medium will be devoid of pantothenate. In other embodiments the bacterium will comprises one or more exogenous genes in a biosynthetic pathway and the medium will be devoid of the product of the corresponding biosynthetic pathway. In some embodiments, the carbon source may comprise an industrial waste stream, such as waste gas from ferrous metal products manufacturing such as steel mill waste gas, waste gas from non-ferrous products manufacturing, waste gas from petroleum refining processes, waste gas from gasification of coal, waste gas from electric power production, waste gas from carbon black production, waste gas from ammonia production, waste gas from methanol production, waste gas from coke manufacturing, and syngas. Automobile exhaust fumes may also be used as a carbon source.

CO Conversion Processes

One embodiment contemplated is a process for converting CO in a CO-containing substrate into higher molecular weight products. The process comprises passing the CO-containing substrate to a bioreactor containing a culture of carboxydotrophic acetogenic bacteria in a culture medium such that the bacteria convert the CO to higher molecule weight products; and recovering the higher molecular weight products from the bioreactor. The carboxydotrophic acetogenic bacteria are genetically engineered to express an enzyme in a biosynthetic pathway of a nutrient that is absent from the culture medium. Optionally added nutrients may be provided to the culture medium for survival and/or growth of the carboxydotrophic acetogenic bacteria. When the carboxydotrophic acetogenic bacteria are genetically engineered to express an enzyme in a biosynthetic pathway of a nutrient, that nutrient is absent from the added nutrients. Optionally the carboxydotrophic acetogenic bacteria are genetically engineered from parental bacteria that are auxotrophic for the nutrient. In one alternative, the higher molecular weight products are selected from the group consisting of alcohols, acids, diols, esters, ketones, and mixtures thereof. In another alternative, the higher molecular weight products are selected from the group consisting of ethanol, acetone, 1-propanol, 2-propanol, 1-butanol, 2-butanol, 1,4-butanediol, 2,3-butaendiol Methyl Ethyl Ketone (MEK), 3-hyrdoxypropionic acid, fatty acid. Terpenoids, 1,3-butadiene, 3-hydroxybutyrate, 2-hydroxyisobutyric acid, acetic acid, and mixtures thereof. Optionally, a selective agent is added to the culture medium, such as an antibiotic to which the desired bacterium is resistant. The antibiotic can be used to inhibit growth of undesired, contaminating microorganisms, or bacteria that have lost the desired biosynthetic enzyme or pathway of enzymes. Notably antibiotic may not be necessary and in some embodiments no exogenous antibiotic is in the culture medium. The biosynthetic enzyme conferring prototrophy may exert sufficient selective pressure to maintain a culture of the desired micoorganisms. This may be a benefit in terms of cost savings, environmental protection, and human health in particular. Typically the culture medium is an aqueous mixture containing dissolved or undissolved gasses. Typically the culturing conditions are maintained between a temperature from about 30° C. and about 37° C. and a pH from about 4 to less than 7. In one embodiment the CO-containing substrate is pre-treated to remove gaseous components other than CO. In some embodiments the nutrient may be produced in excess of the amount required by the bacteria in the culture. In such embodiments that excess nutrient may be collected as a product of the fermentation.

In one embodiment CO in a gaseous CO-containing substrate is convered into higher molecular weight products. The gaseous CO-containing substrate is passed to a bioreactor containing a culture of carboxydotrophic acetogenic bacteria in a culture medium such that the bacteria convert the CO to higher molecule weight products. The higher molecular weight products are recovered from the bioreactor. The carboxydotrophic acetogenic bacteria are genetically engineered to express an enzyme in a biosynthetic pathway of a nutrient that is absent from the culture medium. Moreover, the carboxydotrophic acetogenic bacteria are prototrophic for thiamine and/or pantothenate by virtue of an exogenous thiC gene and/or an exogenous panBCD gene cluster. The nutrient is selected from the group consisting of thiamine and pantothenate.

Compositions as Used in the CO Conversion Processes

Another embodiment is a composition for converting CO in a CO-containing substrate into higher molecular weight products. The composition may comprise carboxydotrophic acetogenic bacteria contained in an aqueous culture medium having a pH from about 4 to less than 7, and one or more nutrients for survival or growth of the carboxydotrophic acetogenic bacteria. The carboxydotrophic acetogenic bacteria are genetically engineered to express an enzyme in a biosynthetic pathway of a nutrient that is absent from the culture media, such as thiamine or pantothenate. The composition may be in a container such as a bioreactor and typically will contain a gaseous carbon source comprising CO.

Other Methods

Another embodiment contemplated is a method for providing a microorganism for use in reducing greenhouse gas emissions from an industrial process. Genomic sequences of the microorganism are analyzed to determine whether a gene encoding an enzyme necessary in a biosynthetic pathway of an essential nutrient is lacking or defective. If a missing or defective enzyme is found, an exogenous (or heterologous) version of the gene is supplied to the microorganism by means of a gene transfer technique so that the microorganism becomes prototrophic for the essential nutrient. The heterologous gene may be from a different species, a different genus, a different phylum, or even a different kingdom. Complementation of the genetic defect or lack will make the microorganism prototrophic.

Yet another embodiment contemplated is a method for transferring an exogenous nucleic acid into a population of carboxydotrophic acetogenic bacteria which are auxotrophic for thiamine and/or pantothenate. The bacteria are transformed with a first nucleic acid which comprises an exogenous thiC gene or an exogenous panBCD gene cluster operably linked to a promoter.

Thiamine prototrophy and/or pantothenate prototrophy is selected for among the transformed bacterial population. Optionally the bacteria may be co-transformed with a second nucleic acid which comprises an exogenous or endogenous gene conferring a desired property when expressed in the bacterium. The desired property need not be selectable. The first and second nucleic acids may be on separate molecules or in the same molecule. Optionally an additional step may be employed to screen prototrophic, transformed bacteria for the presence of the first nucleic acid. Under certain circumstances, it may be necessary and/or desirable to treat the first and second nucleic acids to form methylated first and second nucleic acids prior to the step of co-transforming.

Yet another embodiment uses prototrophy as a selectable marker on its own for transformants, in the absence of any other selective agent such as an antibiotic. The prototrophy may be for a vitamin, as shown below, or any other essential nutrient. The clean selection in the absence of an antibiotic was unexpected. This type of selection can be used in any *Clostridium* described herein, as well as in other gram negative and gram positive bacteria, whether under aerobic or anaerobic growth conditions.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE DRAWINGS

These and other aspects of the present invention, which should be considered in all its novel aspects, will become apparent from the following description, which is given by way of example only, with reference to the accompanying figures, in which.

Figure 1:
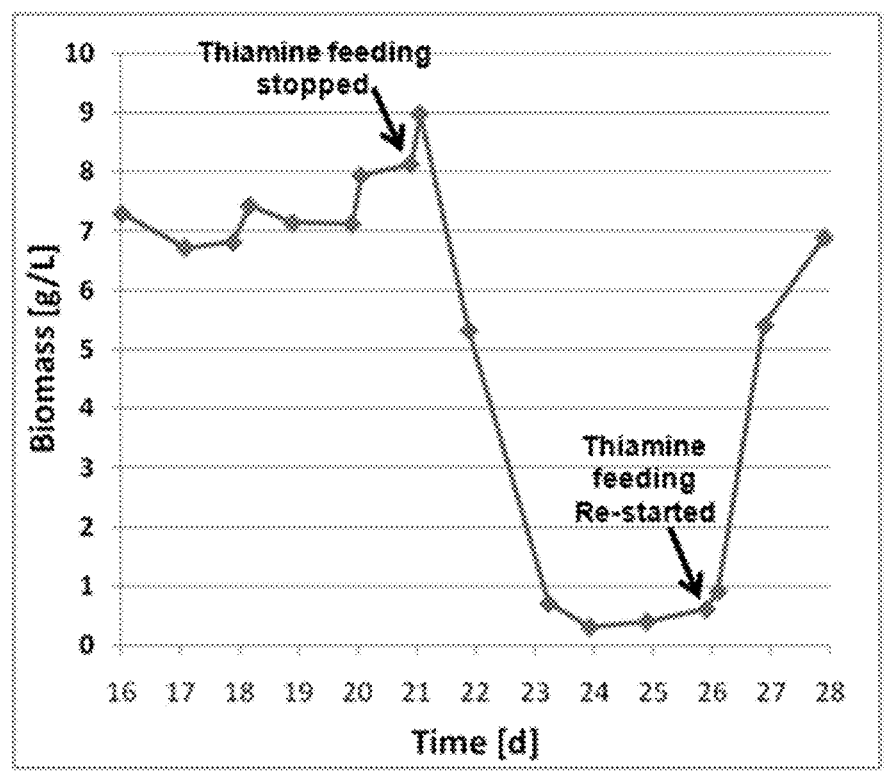
FIG. 1: Growth and metabolite profile of LZ1561 in a continuous culture between days twenty and twenty eight.

A sequence listing is part of this application.

DETAILED DESCRIPTION OF THE INVENTION

The following is a description of the present invention, including preferred embodiments thereof, given in general terms. The invention is further elucidated from the disclosure given under the heading "Examples" herein below, which provides experimental data supporting the invention, specific examples of various aspects of the invention, and means of performing the invention.

The inventors have surprisingly identified that one or more gene(s) in a biosynthesis pathway for a vitamin which is needed for the survival of a microorganism can be used as an effective selective marker to screen for cells transformed with exogenous nucleic acid(s) where the microorganism does not naturally contain or express the one or more gene(s).

This has a number of advantages, including obviating the need for the use of standard selective markers and agents, such as antibiotics, which are expensive, have limitations, and can be toxic to some desirable cells. It also has the benefit of further reducing the cost of the growth and fermentation of recombinant microorganisms as vitamins that would typically need to be added to growth and fermentation media can be omitted. Further, vitamins are themselves a valuable product, so in addition to acting as a selection marker, the vitamins produced may be recovered and sold or used for other purposes.

As referred to herein, a "fermentation broth" is a culture medium comprising at least a nutrient media and bacterial cells.

As referred to herein, a "shuttle microorganism" is a microorganism in which a methyltransferase enzyme is expressed and is distinct from the destination microorganism.

As referred to herein, a "destination microorganism" is a microorganism in which the genes included on an expression construct/vector are expressed and is distinct from the shuttle microorganism.

The term "main fermentation product" is intended to mean the one fermentation product which is produced in the highest concentration and/or yield.

The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated product concentrations, the volume of desired product produced per volume of substrate consumed, the rate of production or level of production of the desired product, and the relative proportion of the desired product produced compared with other by-products of the fermentation.

The phrase "substrate comprising carbon monoxide" and like terms should be understood to include any substrate in which carbon monoxide is available to one or more strains of bacteria for growth and/or fermentation, for example.

The phrase "gaseous substrate comprising carbon monoxide" and like phrases and terms includes any gas which contains a level of carbon monoxide. In certain embodiments the substrate contains at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of $H_2$:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

In the description which follows, embodiments of the invention are described in terms of delivering and fermenting a "gaseous substrate containing CO". However, it should be appreciated that the gaseous substrate may be provided in alternative forms. For example, the gaseous substrate containing CO may be provided dissolved in a liquid. Essentially, a liquid is saturated with a carbon monoxide containing gas and then that liquid is added to the bioreactor. This may be achieved using standard methodology. By way of example, a microbubble dispersion generator (Hensirisak et. al. Scale-up of microbubble dispersion generator for aerobic fermentation; Applied Biochemistry and Biotechnology Volume 101, Number 3/October, 2002) could be used. By way of further example, the gaseous substrate containing CO may be adsorbed onto a solid support. Such alternative methods are encompassed by use of the term "substrate containing CO" and the like.

In particular embodiments of the invention, the CO-containing gaseous substrate is an industrial off or waste gas. "Industrial waste or off gases" should be taken broadly to include any gases comprising CO produced by an industrial process and include gases produced as a result of ferrous metal products manufacturing, non-ferrous products manufacturing, petroleum refining processes, gasification of coal, gasification of biomass, electric power production, carbon black production, and coke manufacturing. Further examples may be provided elsewhere herein.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. In some embodiments the bioreactor may comprise a first growth reactor and a second fermentation reactor. As such, when referring to the addition of substrate to the bioreactor or fermentation reaction it should be understood to include addition to either or both of these reactors where appropriate.

"Exogenous nucleic acids" are nucleic acids which originate outside of the microorganism to which they are introduced. Exogenous nucleic acids may be derived from any appropriate source, including, but not limited to, strains or species of microorganisms which differ from the organism to which they are to be introduced, or they may be artificially or recombinantly created. The exogenous nucleic acids represent nucleic acid sequences not naturally present within the microorganism to which they are to be introduced and allow for the expression of a product not naturally present within the microorganism. The exogenous nucleic acid may be adapted to integrate into the genome of the microorganism to which it is to be introduced or to remain in an extra-chromosomal state. Typically the exogenous nucleic acid is heterologous, coming from a different species, a different genus, or a different phylum or kingdom than the recipient.

It should be appreciated that the invention may be practised using nucleic acids whose sequence varies from the sequences specifically exemplified herein provided they perform substantially the same function. For nucleic acid sequences that encode a protein or peptide this means that the encoded protein or peptide has substantially the same function. For nucleic acid sequences that represent promoter sequences, the variant sequence will have the ability to promote expression of one or more genes. Such nucleic acids may be referred to herein as "functionally equivalent variants". By way of example, functionally equivalent variants of a nucleic acid include allelic variants, fragments of a gene, genes which include mutations (deletion, insertion, nucleotide substitutions and the like) and/or polymorphisms and the like. Homologous genes from other microorganisms may also be considered as examples of functionally equivalent variants of the sequences specifically exemplified herein. These include homologous genes in species such as *E. coli, Bacillus subtilis, Clostridium beijerinckii*, details of which are publicly available on websites such as Genbank or NCBI. The phrase "functionally equivalent variants" should also be taken to include nucleic acids whose sequence varies as a result of codon optimisation for a particular organism. "Functionally equivalent variants" of a nucleic acid herein will preferably have at least approximately 70%, preferably approximately 80%, more preferably approximately 85%, preferably approximately 90%, preferably approximately 95% or greater nucleic acid sequence identity with the nucleic acid identified.

It should also be appreciated that the invention may be practised using polypeptides whose sequence varies from the amino acid sequences specifically exemplified herein. These variants may be referred to herein as "functionally equivalent variants". A functionally equivalent variant of a protein or a peptide includes those proteins or peptides that share at least 40%, preferably 50%, preferably 60%, preferably 70%, preferably 75%, preferably 80%, preferably 85%, preferably 90%, preferably 95% or greater amino acid identity with the protein or peptide identified and has substantially the same function as the peptide or protein of interest. Such variants include within their scope fragments of a protein or peptide wherein the fragment comprises a truncated form of the polypeptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location. Functionally equivalent variants of the specific polypeptides herein should also be taken to include polypeptides expressed by homologous genes in other species of bacteria, for example as exemplified in the previous paragraph.

"Substantially the same function" as used herein is intended to mean that the nucleic acid or polypeptide is able to perform the function of the nucleic acid or polypeptide of which it is a variant. For example, a variant of an enzyme of the invention will be able to catalyse the same reaction as that enzyme. However, it should not be taken to mean that the variant has the same level of activity as the polypeptide or nucleic acid of which it is a variant.

One may assess whether a functionally equivalent variant has substantially the same function as the nucleic acid or polypeptide of which it is a variant using any number of known methods. However, by way of example, the methods outlined in Zhang et al (1997, *J. Bacteriol.*, 179:3030-5), Lawhorn et al. (2004, *Organic & Biomolecular Chemistry*, 2: 2538-46) may be used to assess functionality in respect of ThiC, Powers & Snell (1976, *Biol. Chem.* 251, 3786-3793) may be used to assess functionality in respect of PanB, Cronan et al. (1982, *J. Bacteriol.* 149: 916-922) may be used to assess functionality in respect of PanC, or Williamson (1985, *Methods Enzymol.* 113: 589-595) may be used to assess functionality in respect of PanD, or a genetic screen as outlined by Lawhorn et al. (2004, *J. Soc. Biol. Chem.*, 279: 43555-9) in respect of thiamine genes may be used.

A "parental microorganism" is a microorganism used to generate a recombinant microorganism of the invention. The parental microorganism may be one that occurs in nature (ie a wild type microorganism) or one that has been previously modified but which does not express one or more of the enzymes in the one or more vitamin biosynthesis pathway which is needed for the growth of the microorganism. Accordingly, the recombinant microorganisms of the invention have been modified to express the one or more enzymes that were not expressed in the parental microorganism.

The terms nucleic acid "constructs" or "vectors" and like terms should be taken broadly to include any nucleic acid (including DNA and RNA) suitable for use as a vehicle to transfer genetic material into a cell. The terms should be taken to include plasmids, viruses (including bacteriophage), cosmids and artificial chromosomes. Constructs or vectors may include one or more regulatory elements, an origin of replication, a multicloning site and/or a selectable marker. In one particular embodiment, the constructs or vectors are adapted to allow expression of one or more genes encoded by the construct or vector. Nucleic acid constructs or vectors include naked nucleic acids as well as nucleic acids formulated with one or more agents to facilitate delivery to a cell (for example, liposome-conjugated nucleic acid, an organism in which the nucleic acid is contained).

The invention is applicable to the production of "one or more products" by microbial fermentation. Reference to "one or more products" should be taken broadly to include any product which may be produced by microbial fermentation. However, by way of example, it includes, ethanol, acetate, butanol, isopropanol, one or more vitamins, acetone, 2,3-butane diol.

"Contaminating microorganisms" or "undesirable microorganisms" should be taken broadly to mean any microorganism that is not desired, for what ever reason.

When used in the context of the methods of the invention "preventing growth" and like terms should be taken broadly to include any level of prevention or reduction in the level of growth of one or more microorganism. It should not be construed to mean that growth of a microorganism is completed prevented, inhibited or stopped. However, in a preferred embodiment the growth of the microorganism is substantially prevented.

"Needed for growth" is to be taken to mean that the vitamin is required for a desired level of growth, such that the absence of the vitamin in a media in or on which a microorganism will grow is sufficient to select for a recombinant microorganism (able to make the vitamin) or select against an undesirable or contaminating microorganism. In one embodiment, a vitamin is "essential for growth" of the microorganism. In this case, without the vitamin, a microorganism will not substantially grow, or may die.

"Anaerobe" or "anaerobic microorganism" or like terms should be taken broadly and to include both obligate and facultative anaerobes.

Recombinant Microorganisms

As discussed herein before, the invention provides a recombinant microorganism. The recombinant microorganism comprises at least one exogenous nucleic acid which encodes one or more gene(s) in one or more vitamin biosynthesis pathway which produces a vitamin(s) which is needed for growth of the microorganism. The recombinant microorganism is accordingly able to produce the one or more vitamin(s). The recombinant microorganism is an anaerobe.

The recombinant microorganism is produced from a parental microorganism.

The parental microorganism may be chosen from any microorganism that is lacking the one or more genes in the one or more vitamin biosynthesis pathway.

In one embodiment, the vitamin is chosen from thiamine, pathothenate, riboflavin, nicotinic acid, pyridoxine, biotin, folic acid, and cyanocobalamine. In one particular embodiment, the vitamin is thiamine (B1) or panthothenate (B5).

The one or more enzymes may be any one which is involved in a vitamin biosynthesis pathway. However, by way of example, the one or more enzymes may be chosen from those listed in Tables 1 to 8 below.

TABLE 1

Thiamine (B1) biosynthesis:

cysteine desulfurase [EC: 2.8.1.7]
glycine oxidase [EC: 1.4.3.19]
hydroxyethylthiazole kinase [EC: 2.7.1.50]
hydroxymethylpyrimidine [EC: 2.7.4.7]
nucleoside-triphosphatase [EC: 3.6.1.15]
phosphomethylpyrimidine kinase [EC: 2.7.1.49]
selenocysteine lyase [EC: 4.4.1.16]
sulfur carrier protein ThiS adenylyltransferase [EC: 2.7.7.73]
thiaminase [EC: 3.5.99.2]
thiamine biosynthesis protein ThiC [EC 4.1.99.17]
thiamine biosynthesis protein ThiG
thiamine biosynthesis protein ThiH
thiamine biosynthesis protein ThiI
thiamine kinase [EC: 2.7.1.89]
thiamine pyridinylase [EC: 2.5.1.2]
thiamine pyrophosphokinase [EC: 2.7.6.2]
thiamine-monophosphate kinase [EC: 2.7.4.16]
thiamine-phosphate pyrophosphorylase [EC: 2.5.1.3]
thiamine-triphosphatase [EC: 3.6.1.28]

TABLE 2

Riboflavin (B2) biosynthesis:

GTP cyclohydrolase II [EC: 3.5.4.25]
2,5-diamino-6-(ribosylamino)-4(3H)-pyrimidinone 5'-phosphate reductase [EC: 1.1.1.302]
2-amino-5-formylamino-6-ribosylaminopyrimidin-4(3H)-one 5'-monophosphate deformylase [EC: 3.5.1.102]
3,4-dihydroxy 2-butanone 4-phosphate synthase [EC: 4.1.99.12]
4-phytase/acid phosphatase [EC: 3.1.3.2/3.1.3.26]
5,6-dimethylbenzimidazole synthase [EC: 1.14.99.40]
5-amino-6-(5-phosphoribosylamino)uracil reductase [EC: 1.1.1.193]
6,7-dimethyl-8-ribityllumazine synthase [EC: 2.5.1.78]
acid phosphatase (class A) [EC: 3.1.3.2]
acid phosphatase (class B) [EC: 3.1.3.2]
acid phosphatase [EC: 3.1.3.2]
aquacobalamin reductase/NAD(P)H-flavin reductase [EC: 1.5.1.41/1.16.1.3]
biliverdin reductase/flavin reductase [EC: 1.5.1.30/1.3.1.24]
diaminohydroxyphosphoribosylaminopyrimidine deaminase/5-amino-6-(5-phosphoribosylamino)uracil reductase [EC: 1.1.1.193/3.5.4.26]
diaminohydroxyphosphoribosylaminopyrimidine deaminase [EC: 3.5.4.26]
ectonucleotide pyrophosphatase/phosphodiesterase family member 1/3 [EC: 3.6.1.9/3.1.4.1]
FAD synthetase [EC: 2.7.7.2]
FMN reductase [EC: 1.5.1.38]
GTP cyclohydrolase II [EC: 3.5.4.25]
GTP cyclohydrolase IIa [EC: 3.5.4.29]
low molecular weight phosphotyrosine protein phosphatase [EC: 3.1.3.48/3.1.3.2]
lysophosphatidic acid phosphatase type 6 [EC: 3.1.3.2]
FMN adenylyltransferase [EC: 2.7.7.2]
riboflavin kinase [EC: 2.7.1.26/EC: 2.7.1.161]
riboflavin synthase [EC: 2.5.1.9]
tartrate-resistant acid phosphatase type 5 [EC: 3.1.3.2]
tRNA pseudouridine synthase 8/2,5-diamino-6-(5-phospho-D-ribitylamino)-pyrimidin-4(3H)-one deaminase [EC: 5.4.99.—]
tyrosinase [EC: 1.14.18.1]

TABLE 3

Nicotinic acid (B3) biosynthesis:

5'-nucleotidase [EC: 3.1.3.5]
6-hydroxy-3-succinoylpyridine hydroxylase [EC: 3.7.1.—]
6-hydroxynicotinate 3-monooxygenase [EC: 1.14.13.114]

TABLE 3-continued

Nicotinic acid (B3) biosynthesis:

aldehyde oxidase [EC: 1.2.3.1]
aspartate dehydrogenase [EC: 1.4.1.21]
bifunctional NMN adenylyltransferase/nudix hydrolase
[EC: 3.6.1.— 2.7.7.1]
ectonucleotide pyrophosphatase/phosphodiesterase family
member 1/3 [EC: 3.6.1.9 3.1.4.1]
enamidase [EC: 3.5.2.18]
L-aspartate oxidase [EC: 1.4.3.16]
maleamate amidohydrolase [EC: 3.5.1.107]
maleate isomerase [EC: 5.2.1.1]
NAD(P) transhydrogenase [EC: 1.6.1.1]
NAD(P) transhydrogenase subunit alpha [EC: 1.6.1.2]
NAD(P) transhydrogenase subunit beta [EC: 1.6.1.2]
NAD+ diphosphatase [EC: 3.6.1.22]
NAD+ kinase [EC: 2.7.1.23]
NAD+ nucleosidase [EC: 3.2.2.5]
NAD+ synthase (glutamine-hydrolysing) [EC: 6.3.5.1]
NAD+ synthase [EC: 6.3.1.5]
N-formylmaleamate deformylase [EC: 3.5.1.106]
nicotinamidase [EC: 3.5.1.19]
nicotinamide mononucleotide adenylyltransferase [EC: 2.7.7.18 2.7.7.1]
nicotinamide N-methyltransferase [EC: 2.1.1.1]
nicotinamide phosphoribosyltransferase [EC: 2.4.2.12]
nicotinamide riboside kinase [EC: 2.7.1.22]
nicotinamide-nucleotide adenylyltransferase [EC: 2.7.7.1]
nicotinate phosphoribosyltransferase [EC: 2.4.2.11]
nicotinate-nucleotide adenylyltransferase [EC: 2.7.7.18]
nicotinate-nucleotide pyrophosphorylase (carboxylating) [EC: 2.4.2.19]
purine nucleosidase [EC: 3.2.2.1]
purine-nucleoside phosphorylase [EC: 2.4.2.1]
pyrazinamidase [EC: 3.5.1.—]
quinolinate synthase [EC: 2.5.1.72]
UDP-sugar diphosphatase [EC: 3.6.1.45]

TABLE 4

Panthothenate (B5) biosynthesis:

2-dehydropantoate 2-reductase [EC: 1.1.1.169]
3-methyl-2-oxobutanoate hydroxymethyltransferase PanB [EC: 2.1.2.11]
4'-phosphopantetheinyl transferase [EC: 2.7.8.—]
4-phosphopantoate---beta-alanine ligase [EC: 6.3.2.36]
acetolactate synthase I/II/III large subunit [EC: 2.2.1.6]
acetolactate synthase I/III small subunit [EC: 2.2.1.6]
acetolactate synthase II small subunit [EC: 2.2.1.6]
acyl carrier protein phosphodiesterase [EC: 3.1.4.14]
aspartate 1-decarboxylase PanD [EC: 4.1.1.11]
beta-ureidopropionase [EC: 3.5.1.6]
biotin-[acetyl-CoA-carboxylase] ligase [EC: 6.3.4.15]
branched-chain amino acid aminotransferase [EC: 2.6.1.42]
dephospho-CoA kinase [EC: 2.7.1.24]
dihydropyrimidinase [EC: 3.5.2.2]
dihydropyrimidine dehydrogenase (NADP+) [EC: 1.3.1.2]
dihydroxy-acid dehydratase [EC: 4.2.1.9]
ectonucleotide pyrophosphatase/phosphodiesterase family member 1/3
[EC: 3.6.1.9 3.1.4.1]
holo-[acyl-carrier protein] synthase [EC: 2.7.8.7]
ketol-acid reductoisomerase [EC: 1.1.1.86]
pantetheine hydrolase [EC: 3.5.1.92]
pantetheine-phosphate adenylyltransferase [EC: 2.7.7.3]
pantoate kinase [EC: 2.7.1.169]
pantoate ligase/cytidylate kinase [EC: 2.7.4.14/6.3.2.1]
pantoate--beta-alanine ligase PanC [EC: 6.3.2.1]
phosphopantetheine adenylyltransferase/dephospho-CoA kinase
[EC: 2.7.1.24 2.7.7.3]
phosphopantothenate-cysteine ligase [EC: 6.3.2.5]
phosphopantothenate-cysteine ligase [EC: 6.3.2.5]
phosphopantothenoylcysteine decarboxylase [EC: 4.1.1.36]
type I pantothenate kinase [EC: 2.7.1.33]
type II pantothenate kinase [EC: 2.7.1.33]
type III pantothenate kinase [EC: 2.7.1.33]

TABLE 5

Pyridoxin (B6) biosynthesis:

4-hydroxythreonine-4-phosphate dehydrogenase [EC: 1.1.1.262]
aldehyde oxidase [EC: 1.2.3.1]
D-erythrose 4-phosphate dehydrogenase [EC: 1.2.1.72]
erythronate-4-phosphate dehydrogenase [EC: 1.1.1.290]
glutamine amidotransferase [EC: 2.6.—.—]
phosphoserine aminotransferase [EC: 2.6.1.52]
pyridoxal phosphatase [EC: 3.1.3.74]
pyridoxal phosphate phosphatase [EC: 3.1.3.74]
pyridoxamine 5'-phosphate oxidase [EC: 1.4.3.5]
pyridoxine 4-dehydrogenase [EC: 1.1.1.65]
pyridoxine 5-phosphate synthase [EC: 2.6.99.2]
pyridoxine biosynthesis protein [EC: 4.—.—.—]
pyridoxine kinase [EC: 2.7.1.35]
threonine synthase [EC: 4.2.3.1]

TABLE 6

Biotin (B7) biosynthesis:

6-carboxyhexanoate--CoA ligase [EC: 6.2.1.14]
8-amino-7-oxononanoate synthase [EC: 2.3.1.47]
adenosylmethionine-8-amino-7-oxononanoate aminotransferase
[EC: 2.6.1.62]
biotin synthetase [EC: 2.8.1.6]
biotin-[acetyl-CoA-carboxylase] ligase [EC: 6.3.4.15]
biotinidase [EC: 3.5.1.12]
biotin-protein ligase [EC: 6.3.4.15 6.3.4.11 6.3.4.10 6.3.4.9]
dethiobiotin synthetase [EC: 6.3.3.3]
type III pantothenate kinase [EC: 2.7.1.33]

TABLE 7

Folate (B9)/p-Aminobenzoate (B10) biosynthesis:

2-amino-4-hydroxy-6-hydroxymethyldihydropteridine diphosphokinase
[EC: 2.7.6.3]
4-amino-4-deoxychorismate lyase [EC: 2.6.1.85/EC: 4.1.3.38]
6-pyruvoyl tetrahydrobiopterin synthase [EC: 4.2.3.12]
6-pyruvoyltetrahydropterin 2'-reductase [EC: 1.1.1.220]
alkaline phosphatase [EC: 3.1.3.1]
dihydrofolate reductase [EC: 1.5.1.3]
dihydrofolate synthase/folylpolyglutamate synthase
[EC: 6.3.2.17/6.3.2.12]
dihydromonapterin reductase [EC: 1.5.1.—]
dihydroneopterin aldolase/2-amino-4-hydroxy-6-hydroxymethyl-
dihydropteridine diphosphokinase [EC: 2.7.6.3/4.1.2.25]
dihydroneopterin aldolase [EC: 4.1.2.25]
dihydropteridine reductase [EC: 1.5.1.34]
dihydropteroate synthase [EC: 2.5.1.15]
folylpolyglutamate synthase [EC: 6.3.2.17]
gamma-glutamyl hydrolase [EC: 3.4.19.9]
GTP cyclohydrolase I [EC: 3.5.4.16]
molybdenum cofactor biosynthesis protein
molybdopterin synthase catalytic subunit [EC: 2.—.—.—]
molybdopterin synthase sulfur carrier subunit
para-aminobenzoate synthetase [EC: 2.6.1.85]
para-aminobenzoate synthetase component I [EC: 2.6.1.85]
para-aminobenzoate synthetase component II [EC: 2.6.1.85]
sepiapterin reductase [EC: 1.1.1.153]
thymidylate synthase [EC: 2.1.1.45]

TABLE 8

Cobalamin (B12) biosynthesis 5-aminolevulinate synthase [EC: 2.3.1.37]
5-aminolevulinate:pyruvate aminotransferase [EC 2.6.1.43]
adenosylcobinamide kinase/adenosylcobinamide-phosphate
guanylyltransferase [EC: 2.7.1.156/2.7.7.62]
adenosylcobinamide-GDP ribazoletransferase [EC: 2.7.8.26]
adenosylcobinamide-phosphate synthase [EC: 6.3.1.10]

TABLE 8-continued

Cobalamin (B12) biosynthesis adenosylcobyric acid synthase [EC: 6.3.5.10]
alpha-ribazole phosphatase [EC: 3.1.3.73]
cob(I)alamin adenosyltransferase [EC: 2.5.1.17]
cob(II)yrinic acid a,c-diamide reductase [EC: 1.16.8.1]
cobalt-precorrin 5A hydrolase [EC: 3.7.1.12]
cobalt-precorrin-5B (C1)-methyltransferase [EC: 2.1.1.195]
cobalt-precorrin-7 (C15)-methyltransferase [EC: 2.1.1.196]
cobaltochelatase CobN [EC: 6.6.1.2]
cobyrinic acid a,c-diamide synthase [EC: 6.3.5.9/6.3.5.11]
ferritin [EC: 1.16.3.1]
glutamate-1-semialdehyde 2,1-aminomutase [EC: 5.4.3.8]
glutamyl-tRNA reductase [EC: 1.2.1.70]
glutamyl-tRNA synthetase [EC: 6.1.1.17]
hydroxymethylbilane synthase [EC: 2.5.1.61]
nicotinate-nucleotide-dimethylbenzimidazole phosphoribosyltransferase [EC: 2.4.2.21]
oxygen-independent coproporphyrinogen III oxidase [EC: 1.3.99.22]
porphobilinogen synthase [EC: 4.2.1.24]
precorrin-2 dehydrogenase/sirohydrochlorin ferrochelatase [EC: 1.3.1.76/4.99.1.4]
precorrin-2/cobalt-factor-2 C20-methyltransferase [EC: 2.1.1.130/2.1.1.151]
precorrin-3B synthase [EC: 1.14.13.83]
precorrin-3B C17-methyltransferase [EC: 2.1.1.131]
precorrin-4 C11-methyltransferase [EC: 2.1.1.133]
precorrin-6X reductase [EC: 1.3.1.54]
precorrin-6Y C5,15-methyltransferase [EC: 2.1.1.132]
precorrin-8W decarboxylase [EC: 1.—.—.—]
precorrin-8X methylmutase [EC: 5.4.1.2]
sirohydrochlorin cobaltochelatase [EC: 4.99.1.3]
threonine-phosphate decarboxylase [EC: 4.1.1.81]
uroporphyrinogen decarboxylase [EC: 4.1.1.37]
uroporphyrinogen III methyltransferase/synthase [EC: 2.1.1.107 4.2.1.75]

In one particular embodiment, the parental microorganism lacks one or more of the genes encoding the enzymes thiamine biosynthesis protein ThiC (EC 4.1.99.17), 3-methyl-2-oxobutanoate hydroxymethyltransferase PanB (EC 2.1.2.11), pantoate-beta-alanine ligase PanC (EC 6.3.2.1), and aspartate 1-decarboxylase Pan D (EC 4.1.1.11). In one embodiment, the parental microorganism lacks the gene encoding enzyme ThiC. In another embodiment, the parental microorganism lacks one or more enzymes encoding one or more or all of PanB, PanC and PanD.

While the invention is exemplified herein in respect of certain vitamin biosynthesis pathways, it will be appreciated that other biosynthesis pathways may be used. With knowledge of the present invention, analysis of any sequenced organism can be done using databases like the Kyoto Encyclopedia of Genes and Genomes KEGG (http://www.genome.jp/kegg/; Kanehisa et al., 2012, Nucleic Acids Res. 40, D109-D114; Kanehisa and Goto, 2000, Nucleic Acids Res. 28, 27-30) or BioCyc (http://biocyc.org/; Caspi et al., 2010, Nucleic Acids Res. 38: D473-479) to identify genes which are present or missing from a particular biosynthesis pathway.

The parental microorganism may be chosen from any of the group of anaerobic microorganism, in one embodiment anaerobic bacteria.

In one embodiment, the microorganism is selected from the group comprising the genera *Clostridium*, *Eubacterium*, *Peptostreptococcus*, *Peptococcus*, *Actinomyces*, *Lactobacillus*, *Bifidobacterium*, *Propionibacterium*, *Bacteroides*, *Fusobacterium*, *Campylobacter*, or *Veillonella*.

In one particular embodiment, the parental microorganism is selected from the group of carboxydotrophic acetogenic bacteria. In certain embodiments the microorganism is selected from the group comprising *Clostridium autoethanogenum*, *Clostridium ljungdahlii*, *Clostridium ragsdalei*, *Clostridium carboxidivorans*, *Clostridium drakei*, *Clostridium scatologenes*, *Clostridium aceticum*, *Clostridium formicoaceticum*, *Clostridium magnum*, *Butyribacterium methylotrophicum*, *Acetobacterium woodii*, *Alkalibaculum bacchii*, *Blautia producta*, *Eubacterium limosum*, *Moorella thermoacetica*, *Moorella thermautotrophica*, *Sporomusa ovata*, *Sporomusa silvacetica*, *Sporomusa sphaeroides*, *Oxobacter pfennigii*, and *Thermoanaerobacter kiuvi*.

In one particular embodiment, the parental microorganism is selected from the cluster of ethanologenic, acetogenic Clostridia comprising the species *C. autoethanogenum*, *C. ljungdahlii*, and *C. ragsdalei* and related isolates. These include but are not limited to strains *C. autoethanogenum* JAI-1$^T$ (DSM10061) [Abrini J, Naveau H, Nyns E-J: *Clostridium autoethanogenum*, sp. nov., an anaerobic bacterium that produces ethanol from carbon monoxide. Arch Microbiol 1994, 4: 345-351], *C. autoethanogenum* LBS1560 (DSM19630) [Simpson S D, Forster R L, Tran P T, Rowe M J, Warner I L: Novel bacteria and methods thereof. International patent 2009, WO/2009/064200], *C. autoethanogenum* LBS1561 (DSM23693), *C. ljungdahlii* PETC$^T$ (DSM13528=ATCC 55383) [Tanner R S, Miller L M, Yang D: *Clostridium ljungdahlii* sp. nov., an Acetogenic Species in Clostridial rRNA Homology Group I. Int J Syst Bacteriol 1993, 43: 232-236], *C. ljungdahlii* ERI-2 (ATCC 55380) [Gaddy J L: *Clostridium* stain which produces acetic acid from waste gases. US patent 1997, U.S. Pat. No. 5,593,886], *C. ljungdahlii* C-01 (ATCC 55988) [Gaddy J L, Clausen E C, Ko C-W: Microbial process for the preparation of acetic acid as well as solvent for its extraction from the fermentation broth. US patent, 2002, U.S. Pat. No. 6,368,819], *C. ljungdahlii* 0-52 (ATCC 55989) [Gaddy J L, Clausen E C, Ko C-W: Microbial process for the preparation of acetic acid as well as solvent for its extraction from the fermentation broth. US patent, 2002, U.S. Pat. No. 6,368,819], *C. ragsdalei* P11$^T$ (ATCC BAA-622) [Huhnke R L, Lewis R S, Tanner R S: Isolation and Characterization of novel Clostridial Species. International patent 2008, WO 2008/028055], related isolates such as "*C. coskatii*" [Zahn et al—Novel ethanologenic species *Clostridium coskatii* (US Patent Application number US20110229947)] and "*Clostridium* sp." (Tyurin et al., 2012, 1 Biotech Res. 4: 1-12), or mutated strains such as *C. ljungdahlii* OTA-1 (Tirado-Acevedo O. Production of Bioethanol from Synthesis Gas Using *Clostridium ljungdahlii*. PhD thesis, North Carolina State University, 2010). These strains form a subcluster within the Clostridial rRNA cluster I, and their 16S rRNA gene is more than 99% identical with a similar low GC content of around 30%. However, DNA-DNA reassociation and DNA fingerprinting experiments showed that these strains belong to distinct species [Huhnke R L, Lewis R S, Tanner R S: Isolation and Characterization of novel Clostridial Species. International patent 2008, WO 2008/028055].

All species of this cluster have a similar morphology and size (logarithmic growing cells are between 0.5-0.7×3-5 µm), are mesophilic (optimal growth temperature between 30-37° C.) and strictly anaerobe [Tanner R S, Miller L M, Yang D: *Clostridium ljungdahlii* sp. nov., an Acetogenic Species in Clostridial rRNA Homology Group I. Int J Syst Bacteriol 1993, 43: 232-236; Abrini J, Naveau H, Nyns E-J: *Clostridium autoethanogenum*, sp. nov., an anaerobic bacterium that produces ethanol from carbon monoxide. Arch Microbiol 1994, 4: 345-351; Huhnke R L, Lewis R S, Tanner R S: Isolation and Characterization of novel Clostridial Species. International patent 2008, WO 2008/028055]. Moreover, they all share the same major phylogenetic traits, such as same pH range (pH 4-7.5, with an optimal initial pH of 5.5-6), strong autotrophic growth on CO containing gases with similar growth rates, and a similar metabolic profile with ethanol and acetic acid as main fermentation end product, and small amounts of 2,3-butanediol and lactic acid formed under certain conditions. [Tanner R S, Miller L M, Yang D: *Clostridium ljungdahlii* sp. nov., an Acetogenic Species in Clostridial rRNA Homology Group I. Int J Syst Bacteriol 1993, 43: 232-236; Abrini J, Naveau H, Nyns E-J: *Clostridium autoethanogenum*, sp. nov., an anaerobic bacterium that produces ethanol from carbon monoxide. Arch Microbiol 1994, 4: 345-351; Huhnke R L, Lewis R S, Tanner R S: Isolation and Characterization of novel Clostridial Species. International patent 2008, WO 2008/028055]. Indole production was observed with all three species as well. However, the species differentiate in substrate utilization of various sugars (e.g. rhamnose, arabinose), acids (e.g. gluconate, citrate), amino acids (e.g. arginine, histidine), or other substrates (e.g. betaine, butanol). Moreover some of the species were found to be auxotroph to certain vitamins (e.g. thiamine, biotin) while others were not.

The strains of this cluster are defined by common characteristics, having both a similar genotype and phenotype, and they all share the same mode of energy conservation and fermentative metabolism. The strains of this cluster lack cytochromes and conserve energy via an Rnf complex.

All strains of this cluster have a genome size of around 4.2 MBp (Köpke et al., 2010) and a GC composition of around 32% mol (Abrini et al., 1994; Köpke et al., 2010; Tanner et al., 1993) (WO 2008/028055; US patent 2011/0229947), and conserved essential key gene operons encoding for enzymes of Wood-Ljungdahl pathway (Carbon monoxide dehydrogenase, Formyl-tetrahydrofolate synthetase, Methylene-tetrahydrofolate dehydrogenase, Formyl-tetrahydrofolate cyclohydrolase, Methylene-tetrahydrofolate reductase, and Carbon monoxide dehydrogenase/Acetyl-CoA synthase), hydrogenase, formate dehydrogenase, Rnf complex (rnfCDGEAB), pyruvate:ferredoxin oxidoreductase, aldehyde:ferredoxin oxidoreductase (Köpke et al., 2010, 2011). The organization and number of Wood-Ljungdahl pathway genes, responsible for gas uptake, has been found to be the same in all species, despite differences in nucleic and amino acid sequences (Köpke et al., 2011).

Reduction of carboxylic acids into their corresponding alcohols has been shown in a range of these organisms (Perez, Richter, Loftus, & Angenent, 2012).

The traits described are therefore not specific to one organism like *C. autoethanogenum* or *C. ljungdahlii*, but rather general traits for carboxydotrophic, ethanol-synthesizing Clostridia. Thus, the invention can be anticipated to work across these strains, although there may be differences in performance.

The recombinant carboxydotrophic acetogenic microorganisms of the invention may be prepared from a parental carboxydotrophic acetogenic microorganism and one or more exogenous nucleic acids using any number of techniques known in the art for producing recombinant microorganisms. By way of example only, transformation (including transduction or transfection) may be achieved by electroporation, electrofusion, ultrasonication, polyethylene glycol-mediated transformation, conjugation, or chemical and natural competence. Suitable transformation techniques are described for example in Sambrook J, Fritsch E F, Maniatis T: Molecular Cloning: A laboratory Manual, Cold Spring Harbour Laboratory Press, Cold Spring Harbour, 1989.

Electroporation has been described for several carboxydotrophic acetogens as *C. ljungdahlii* (Köpke et al., 2010; Leang, Ueki, Nevin, & Lovley, 2012) (PCT/NZ2011/000203; WO2012/053905), *C. autoethanogenum* (PCT/NZ2011/000203; WO2012/053905), *Acetobacterium woodii* (Strätz, Sauer, Kuhn, & Dune, 1994) or *Moorella thermoacetica* (Kita et al., 2012) and is a standard method used in many Clostridia such as *C. acetobutylicum* (Mermelstein, Welker, Bennett, & Papoutsakis, 1992), *C. cellulolyticum* (Jennert, Tardif, Young, & Young, 2000) or *C. thermocellum* (MV Tyurin, Desai, & Lynd, 2004).

Electrofusion has been described for acetogenic *Clostridium* sp. MT351 (Tyurin and Kiriukhin, 2012).

Prophage induction has been described for carboxydotrophic acetogen as well in case of *C. scatologenes* (Prasanna Tamarapu Parthasarathy, 2010, Development of a Genetic Modification System in *Clostridium scatologenes* ATCC 25775 for Generation of Mutants, Masters Project Western Kentucky University).

Conjugation has been described as method of choice for acetogen *Clostridium difficile* (Herbert, O'Keeffe, Purdy, Elmore, & Minton, 2003) and many other Clostridia including *C. acetobuylicum* (Williams, Young, & Young, 1990). In one embodiment, the parental strain uses CO as its sole carbon and energy source.

In one embodiment the parental microorganism is *Clostridium autoethanogenum* or *Clostridium ljungdahlii*. In one particular embodiment, the microorganism is *Clostridium autoethanogenum* DSM23693. In another particular embodiment, the microorganism is *Clostridium ljungdahlii* DSM13528 (or ATCC55383).

In one particular embodiment, the parental microorganism is *Clostridium autoethanogenum*, the biosynthesis pathway is for thiamine or panthothenate and the parental microorganism lacks the genes thiC or one or more of panB, panC and panD.

In one particular embodiment, the recombinant microorganism is adapted to express one or more enzymes in a vitamin biosynthesis pathway which produces a vitamin(s) which is needed for the growth of the microorganism and which are not naturally present in the parental microorganism.

The microorganism may be adapted to express the one or more enzymes by any number of recombinant methods including, for example, introducing an exogenous nucleic acid encoding and adapted to express an enzyme not naturally present within the parental microorganism.

The vitamins and enzymes of use in the recombinant microorganisms of the invention are defined elsewhere herein.

In one embodiment, the microorganism comprises one or more exogenous nucleic acids encoding and adapted to express one or more of the enzymes referred to elsewhere herein. In one embodiment, the microorganisms comprise one or more exogenous nucleic acid encoding and adapted to express at least two of the enzymes. In other embodiments, the microorganism comprises one or more exogenous nucleic acid encoding and adapted to express 3, 4, 5, or 6 of the enzymes.

The microorganism may comprise one or more exogenous nucleic acids. Where it is desirable to transform the parental microorganism with two or more genetic elements (such as) they may be contained on one or more exogenous nucleic acids.

In one embodiment, the one or more exogenous nucleic acid is a nucleic acid construct or vector, in one particular embodiment a plasmid, encoding one or more of the enzymes referred to herein in any combination.

The exogenous nucleic acids may remain extra-chromosomal upon transformation of the parental microorganism or preferably intergrate into the genome of the parental microorganism. Accordingly, they may include additional nucleotide sequences adapted to assist integration (for example, a region which allows for homologous recombination and targeted integration into the host genome) or expression and replication of an extrachromosomal construct (for example, origin of replication, promoter and other regulatory elements or sequences).

In one embodiment, the exogenous nucleic acids encoding one or enzymes as mentioned herein before will further comprise a promoter adapted to promote expression of the one or more enzymes encoded by the exogenous nucleic acids. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster and Phosphotransacetylase/Acetate kinase promoters. It will be appreciated by those of skill in the art that other promoters which can direct expression, preferably a high level of expression under appropriate fermentation conditions, would be effective as alternatives to the exemplified embodiments.

In one embodiment, the exogenous nucleic acid is an expression plasmid.

Nucleic Acids

The invention also provides nucleic acids and nucleic acid constructs of use in generating a recombinant microorganism of the invention.

The nucleic acids comprise sequences encoding one or more enzymes of one or more vitamin biosynthesis pathway which when expressed in a microorganism allows the microorganism to produce a vitamin which is needed for the growth of the microorganism. In one particular embodiment, the invention provides a nucleic acid encoding two or more enzymes. In one embodiment, the nucleic acids of the invention encode 3, 4, 5 or 6 such enzymes.

A nucleic acid of the invention encodes one or more enzyme in a vitamin biosynthesis pathway. In one particular embodiment, a nucleic acid of the invention encodes one or more enzyme in the biosynthesis pathway of one or more of Thiamine, pathothenate, riboflavin, nicotinic acid, pyridoxine, biotin, folic acid, and cyanocobalamine. In one embodiment, a nucleic acid of the invention encodes one or more of the enzymes listed in tables 3 to 10 herein before.

In one particular embodiment, a nucleic acid of the invention encodes one or more enzymes in the thiamine biosynthesis pathway. In one embodiment, the nucleic acid encodes ThiC.

In another embodiment, a nucleic acid of the invention encodes one or more enzymes in the panthothenate pathway. In one particular embodiment, a nucleic acid encodes one or more or all of panB, panC or panD.

Skilled persons will readily appreciate nucleic acids sequences encoding the enzymes or functionally equivalent variants thereof which are of use in the invention, having regard to the information contained herein, in GenBank and other databases, and the genetic code. However, by way of example only, exemplary amino acid sequences and nucleic acid sequences encoding enzymes of relevance to the invention may be obtained from databases such as the NCBI, KEGG and BRENDA databases, for example.

By way of example only, in one embodiment, ThiC has the sequence of SEQ ID No. 3, or is a functionally equivalent variant thereof. By way of further example, in one embodiment, panB has the sequence of YP_001309722.1 (GenBank) or is a functionally equivalent variant thereof, panC has the sequence of YP_001309721.1 (GenBank) or is a functionally equivalent variant thereof, and panD has the sequence of YP_001309720.1 (GenBank) or is a functionally equivalent variant thereof.

Again, by way of example only, in one embodiment, a nucleic acid encoding ThiC has the sequence of SEQ ID No. 2, or is a functionally equivalent variant thereof. By way of further example, in one embodiment, a nucleic acid encoding panB has the sequence of Cbei_2610; Gene ID: 5293811 or is a functionally equivalent variant thereof, a nucleic acid encoding panC has the sequence of Cbei_2609; Gene ID: 5293810 or is a functionally equivalent variant thereof, and a nucleic acid encoding panD has the sequence of Cbei_2608; Gene ID: 5293809 or is a functionally equivalent variant thereof.

In one embodiment, the nucleic acids of the invention will further comprise a promoter. In one embodiment, the promoter allows for constitutive expression of the genes under its control. However, inducible promoters may also be employed. Persons of skill in the art will readily appreciate promoters of use in the invention. Preferably, the promoter can direct a high level of expression under appropriate fermentation conditions. In a particular embodiment a Wood-Ljungdahl cluster promoter is used. In another embodiment, a Phosphotransacetylase/Acetate kindase promoter is used. In another embodiment a pyruvate:ferredoxin oxidoreductase promoter, an Rnf complex operon promoter or an ATP synthase operon promoter. In one particular embodiment, the promoter is from *C. autoethanogenum*.

The nucleic acids of the invention may remain extra-chromosomal upon transformation of a parental microorganism or may preferably be adapted for intergration into the genome of the microorganism. Accordingly, nucleic acids of the invention may include additional nucleotide sequences adapted to assist integration (for example, a region which allows for homologous recombination and targeted integration into the host genome) or stable expression and replication of an extrachromosomal construct (for example, origin of replication, promoter and other regulatory sequences).

In one embodiment, the nucleic acid is nucleic acid construct or vector. In one particular embodiment, the nucleic acid construct or vector is an expression construct or vector, however other constructs and vectors, such as those used for cloning are encompassed by the invention. In one particular embodiment, the expression construct or vector is a plasmid.

It will be appreciated that an expression construct/vector of the present invention may contain any number of regulatory elements in addition to the promoter as well as additional genes suitable for expression of further proteins if desired. In one embodiment the expression construct/vector includes one promoter. In another embodiment, the expression construct/vector includes two or more promoters. In one particular embodiment, the expression construct/vector includes one promoter for each gene to be expressed. In one embodiment, the expression construct/vector includes one or more ribosomal binding sites, preferably a ribosomal binding site for each gene to be expressed.

It will be appreciated by those of skill in the art that the nucleic acid sequences and construct/vector sequences described herein may contain standard linker nucleotides such as those required for ribosome binding sites and/or restriction sites. Such linker sequences should not be interpreted as being required and do not provide a limitation on the sequences defined.

Nucleic acids and nucleic acid constructs, including expression constructs/vectors of the invention may be constructed using any number of techniques standard in the art. For example, chemical synthesis or recombinant techniques may be used. Such techniques are described, for example, in Sambrook et al (Molecular Cloning: A laboratory manual, Cold Spring Harbor Laboratory Press, Cold Spring Harbor, N.Y., 1989). Further exemplary techniques are described in the Examples section herein after. Essentially, the individual genes and regulatory elements will be operably linked to one another such that the genes can be expressed to form the desired proteins. Suitable vectors for use in the invention will be appreciated by those of ordinary skill in the art. However, by way of example, the following vectors may be suitable: pMTL80000 vectors, pIMP1, pJIR750, and the plasmids exemplified in the Examples section herein after.

It should be appreciated that nucleic acids of the invention may be in any appropriate form, including RNA, DNA, or cDNA.

The invention also provides host organisms, particularly microorganisms, and including viruses, bacteria, and yeast, comprising any one or more of the nucleic acids described herein.

The one or more exogenous nucleic acids may be delivered to a parental microorganism as naked nucleic acids or may be formulated with one or more agents to facilitate the transformation process (for example, liposome-conjugated nucleic acid, an organism in which the nucleic acid is contained). The one or more nucleic acids may be DNA, RNA, or combinations thereof, as is appropriate. Restriction inhibitors may be used in certain embodiments; see, for example Murray, N. E. et al. (2000) *Microbial. Molec. Biol. Rev.* 64, 412.)

The microorganisms of the invention may be prepared from a parental microorganism and one or more exogenous nucleic acids using any number of techniques known in the art for producing recombinant microorganisms. By way of example only, transformation (including transduction or transfection) may be achieved by electroporation, ultrasonication, polyethylene glycol-mediated transformation, chemical or natural competence, or conjugation. Suitable transformation techniques are described for example in, Sambrook J, Fritsch E F, Maniatis T: Molecular Cloning: A laboratory Manual, Cold Spring Harbour Labrotary Press, Cold Spring Harbour, 1989.

In certain embodiments, due to the restriction systems which are active in the microorganism to be transformed, it is necessary to methylate the nucleic acid to be introduced into the microorganism. This can be done using a variety of techniques, including those described below, and further exemplified in the Examples section herein after.

By way of example, in one embodiment, a recombinant microorganism of the invention is produced by a method comprises the following steps:
a. introduction into a shuttle microorganism of (i) of an expression construct/vector as described herein and (ii) a methylation construct/vector comprising a methyltransferase gene; expression of the methyltransferase gene;
b. isolation of one or more constructs/vectors from the shuttle microorganism; and,
c. introduction of the one or more construct/vector into a destination microorganism.

In one embodiment, the methyltransferase gene of step B is expressed constitutively. In another embodiment, expression of the methyltransferase gene of step B is induced.

The shuttle microorganism is a microorganism, preferably a restriction negative microorganism, that facilitates the methylation of the nucleic acid sequences that make up the expression construct/vector. In a particular embodiment, the shuttle microorganism is a restriction negative *E. coli, Bacillus subtillis*, or *Lactococcus lactis*.

The methylation construct/vector comprises a nucleic acid sequence encoding a methyltransferase.

Once the expression construct/vector and the methylation construct/vector are introduced into the shuttle microorganism, the methyltransferase gene present on the methylation construct/vector is induced. Induction may be by any suitable promoter system although in one particular embodiment of the invention, the methylation construct/vector comprises an inducible lac promoter and is induced by addition of lactose or an analogue thereof, more preferably isopropyl-β-D-thio-galactoside (IPTG). Other suitable promoters include the ara, tet, or T7 system. In a further embodiment of the invention, the methylation construct/vector promoter is a constitutive promoter.

In a particular embodiment, the methylation construct/vector has an origin of replication specific to the identity of the shuttle microorganism so that any genes present on the methylation construct/vector are expressed in the shuttle microorganism. Preferably, the expression construct/vector has an origin of replication specific to the identity of the destination microorganism so that any genes present on the expression construct/vector are expressed in the destination microorganism.

Expression of the methyltransferase enzyme results in methylation of the genes present on the expression construct/vector. The expression construct/vector may then be isolated from the shuttle microorganism according to any one of a number of known methods. By way of example only, the methodology described in the Examples section described hereinafter may be used to isolate the expression construct/vector.

In one particular embodiment, both construct/vector are concurrently isolated.

The expression construct/vector may be introduced into the destination microorganism using any number of known methods. However, by way of example, the methodology described in the Examples section hereinafter may be used. Since the expression construct/vector is methylated, the nucleic acid sequences present on the expression construct/vector are able to be incorporated into the destination microorganism and successfully expressed.

It is envisaged that a methyltransferase gene may be introduced into a shuttle microorganism and over-expressed. Thus, in one embodiment, the resulting methyltransferase enzyme may be collected using known methods and used in vitro to methylate an expression plasmid. The expression construct/vector may then be introduced into the destination microorganism for expression. In another embodiment, the methyltransferase gene is introduced into the genome of the shuttle microorganism followed by introduction of the expression construct/vector into the shuttle microorganism, isolation of one or more constructs/vectors from the shuttle microorganism and then introduction of the expression construct/vector into the destination microorganism.

It is envisaged that the expression construct/vector and the methylation construct/vector as defined above may be combined to provide a composition of matter. Such a composition has particular utility in circumventing restriction barrier mechanisms to produce the recombinant microorganisms of the invention.

In one particular embodiment, the expression construct/vector and/or the methylation construct/vector are plasmids.

Persons of ordinary skill in the art will appreciate a number of suitable methyltransferases of use in producing the microorganisms of the invention. However, by way of example the *Bacillus subtilis* phage ΦT1 methyltransferase and a methyltransferase having the sequence of SEQ ID 14 or a functionally equivalent variant thereof may be used. Nucleic acids encoding suitable methyltransferases will be readily appreciated having regard to the sequence of the desired methyltransferase and the genetic code. In one embodiment, the nucleic acid encoding a methyltransferase is as for SEQ ID 15 or it is a functionally equivalent variant thereof.

Any number of constructs/vectors adapted to allow expression of a methyltransferase gene may be used to generate the methylation construct/vector. However, by way of example, the plasmid described in the Examples section hereinafter may be used.

Methods of Production

The invention provides a method for the production of one or more desirable products by microbial fermentation of a substrate using a recombinant microorganism of the invention.

Any substrate which is appropriate for anaerobic fermentation may be used for the fermentation, including, for example, carbohydrates, sugars, substrates comprising CO, substrates comprising carbon dioxide and hydrogen, glycerol, fatty acids, starch, molasses, pentoses and hexoses sugars, biomass. In one embodiment, the substrate is a substrate comprising CO. In this embodiment, the methods of the invention may be used to reduce the total atmospheric carbon emissions from an industrial process.

Preferably, the fermentation comprises the steps of fermenting a substrate in a bioreactor to produce the one or more products using a recombinant microorganism of the invention.

In one embodiment the method comprises the steps of:
(a) providing a substrate to a bioreactor containing a culture of one or more microorganism of the invention; and
(b) anaerobic fermentation of the culture in the bioreactor to produce the one or more products.

In one embodiment the method comprises the steps of:
(a) capturing CO-containing gas produced as a result of the industrial process, before the gas is released into the atmosphere;
(b) the anaerobic fermentation of the CO-containing gas to produce the one or more products by a culture containing one or more microorganism of the invention.

In an embodiment of the invention, the gaseous substrate fermented by the microorganism is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. The CO may be a component of syngas (gas comprising carbon monoxide and hydrogen). The CO produced from industrial processes is normally flared off to produce $CO_2$ and therefore the invention has particular utility in reducing $CO_2$ greenhouse gas emissions and producing butanol for use as a biofuel. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

It will be appreciated that for growth of the bacteria and substrate to the one or more product(s) to occur, in addition to the substrate, a suitable liquid nutrient medium will need to be fed to the bioreactor. The substrate and media may be fed to the bioreactor in a continuous, batch or batch fed fashion. A nutrient medium will contain a number of compounds sufficient to permit survival and/or growth of the micro-organism used, as known in the art. Suitable anaerobic and aerobic fermentation media are known in the art. For example, suitable media are described Biebel (2001). However, the present invention offers the advantage of not having to include in the media one or more vitamin, as the recombinant microorganism is able to produce it. Accordingly, minimal media may be used, reducing costs. In addition, growth and fermentation of recombinant microorganisms typically involves the addition to the media of a selection compound, typically one or more antibiotic, so that the recombinant microorganism is selected for and any contaminating microorganisms do not survive. The use of antibiotics increases the cost of fermentation, and there may be other downsides such as toxicity. The present invention obviates the need for antibiotics. In one embodiment of the invention the media is as described in the Examples section herein after.

The fermentation should desirably be carried out under appropriate conditions for the substrate-to-the one or more product(s) fermentation to occur. Reaction conditions that should be considered include pressure, temperature, gas flow rate, liquid flow rate, media pH, media redox potential, agitation rate (if using a continuous stirred tank reactor), inoculum level, maximum substrate concentrations to ensure that it does not become limiting, and maximum product concentrations to avoid product inhibition.

Where a substrate comprising CO is used, it is often desirable to increase the CO concentration of the substrate stream (or CO partial pressure in a gaseous substrate) and thus increase the efficiency of fermentation reactions where CO is a substrate. Operating at increased pressures allows a significant increase in the rate of CO transfer from the gas phase to the liquid phase where it can be taken up by the micro-organism as a carbon source for the production of the one or more products. This in turn means that the retention time (defined as the liquid volume in the bioreactor divided by the input gas flow rate) can be reduced when bioreactors are maintained at elevated pressure rather than atmospheric pressure. The optimum reaction conditions will depend partly on the particular micro-organism of the invention used. However, in general, it is preferred that the fermentation be performed at pressure higher than ambient pressure. Also, since a given CO-to-the one or more product(s) conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

By way of example, the benefits of conducting a gas-to-ethanol fermentation at elevated pressures has been described. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that the product is consumed by the culture.

The composition of gas streams used to feed a fermentation reaction can have a significant impact on the efficiency and/or costs of that reaction. For example, 02 may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

In certain embodiments a culture of a bacterium of the invention is maintained in an aqueous culture medium (which does not include one or more vitamins in accordance with the invention). Preferably the aqueous culture medium is a minimal microbial growth medium. Suitable media are known in the art and described for example in U.S. Pat. Nos. 5,173,429 and 5,593,886 and WO 02/08438, and as described in the Examples section herein after.

The one or more products may be recovered from the fermentation broth by methods known in the art, such as fractional distillation or evaporation, pervaporation, gas stripping and extractive fermentation, including for example, liquid-liquid extraction.

In certain preferred embodiments of the invention, the one or more products are recovered from the fermentation broth by continuously removing a portion of the broth from the bioreactor, separating microbial cells from the broth (conveniently by filtration), and recovering one or more products from the broth. Alcohols may conveniently be recovered for example by distillation. Acetone may be recovered for example by distillation. Any acids produced may be recovered for example by adsorption on activated charcoal. The separated microbial cells are preferably returned to the fermentation bioreactor. The cell free permeate remaining after any alcohol(s) and acid(s) have been removed is also preferably returned to the fermentation bioreactor.

Vitamins may be recovered using any appropriate means. However, by way of example they may be recovered by concentration and drying of the cells (e.g. centrifugation or spray drying) with subsequent extraction (e.g. in alcohol with purification and filtration using chromatography or simply by differential centrifugation) and crystallization (Survase et al., 2006, *Food Technol. Biotechnol.* 44: 381-96).

In one embodiment, the one or more product (in one particular embodiment one or more vitamin) is recovered from the fermentation and passed to one or more further bioreactor to support the growth of, or support the fermentation of a substrate by, one or more second microorganism.

In one embodiment, the one or more second microorganism is a microorganism which is unable to produce, or unable to produce at sufficient levels, of the one or more vitamin(s) and requires its growth or fermentation media to be supplemented with the one or more vitamin(s) to ensure or maintain growth or fermentation, or to increase the efficiency of growth or fermentation.

The one or more product recovered from the first fermentation may be passed to one or more further bioreactor using any suitable conduit.

In one embodiment, the methods of the invention may further comprise fermentation of a substrate by the one or more second microorganism to produce one or more products. In one embodiment, the one or more products may then be recovered from the fermentation broth.

Methods of Selection

The invention also provides a method for the selection of a microorganism A in a mixed population of microorganisms, wherein microorganism A is a recombinant microorganism comprising at least one exogenous nucleic acid which is adapted to express one or more enzymes in one or more vitamin biosynthesis pathway which produces one or more vitamin(s) which is needed for the growth of the mixed population of microorganisms.

The method comprises subjecting the mixed population of microorganisms to culture conditions including a media which lacks the one or more vitamin(s) which is needed for the growth of the microorganisms. Those microorganisms not able to produce the one or more vitamin(s), will not grow or will be selected against.

In other embodiments, the one or more of the enzyme is as herein before described. The one or more vitamin is as herein before described. In one particular embodiment, the one or more vitamin is chosen from thiamine, pathothenate, riboflavin, nicotinic acid, pyridoxine, biotin, folic acid, and/or cyanocobalamine.

The "culture conditions" may be any suitable conditions which allow for at least the maintenance of a culture of microorganism A and include conditions suitable for growth and/or fermentation. Skilled persons will appreciate suitable conditions, having regard to the nature of the microorganism, and the information contained herein. However, by way of example, growth conditions include suitable environmental conditions including pH, presence or absence of oxygen and other gases, salinity, temperature and the like.

Any suitable media may be used, provided it lacks the one or more vitamin needed for the growth of the microorganisms (which can be produced by microorganism A) as described herein before. Skilled persons will readily appreciate a variety of appropriate media. However, in one embodiment, the media is a minimal media.

While the invention overcomes the need to use alternative selection means or supplement media with ingredients such as antibiotics, these methods could be combined with the current invention if desired.

The method of this aspect of the invention may be useful to distinguish between recombinant and non-recombinant microorganisms during the process of producing recombinant microorganisms—for example, distinguishing successfully transformed bacteria during a transformation process.

The method may also be useful for the purpose of selecting against contaminating microorganisms during laboratory or commercial scale culturing of microorganisms and/or fermentation reactions. Without selection measures, undesirable microrgansisms may grow to the detriment of a desired microorganism, or otherwise affect the efficiency of the culture or fermentation reaction.

Accordingly, the invention also provides a means of preventing the growth of one or more undesirable microorganism in a microbial culture or a fermentation broth, wherein the microbial culture or fermentation broth comprises microorganism A and a nutrient media, wherein microorganism A is a recombinant microorganism comprising at least one exogenous nucleic acid which is adapted to express one or more enzymes in one or more vitamin biosynthesis pathway which produces one or more vitamin(s) which is needed for the growth of microorganism A and the undesirable microorganism(s) such that the microorganism A can produce the one or more vitamin(s), wherein the media lacks the one or more vitamin(s).

The invention further provides a method for the selective growth or culture of a microorganism A, and wherein microorganism A is a recombinant microorganism comprising at least one exogenous nucleic acid which is adapted to express one or more enzymes in one or more vitamin biosynthesis pathway which produces one or more vitamin(s) which are needed for the growth of the microorganism, such that the microorganism A can produce the one or more vitamin(s), and wherein the growth or culture media lacks the one or more vitamin(s).

In one embodiment, the conditions select against the growth of one or more undesirable microorganism(s).

In another aspect, the invention provides a method for the production of one or more products by microbial fermentation of a substrate by a microorganism A, wherein microorganism A is a recombinant microorganism comprising at least one exogenous nucleic acid which is adapted to express one or more enzymes in one or more vitamin biosynthesis pathway which produces one or more vitamin(s) which are needed for the growth of the microorganism, such that the microorganism A can produce the one or more vitamin(s), and wherein fermentation occurs in or on a growth media which lacks the one or more vitamin(s).

In one embodiment, the conditions select for growth of microorganism A and against the growth of one or more undesirable microorganism(s).

It should be appreciated that the microorganisms, including recombinant microorganism A, of this aspect of the invention may be chosen from any microorganism of interest, and are not limited to anaerobes. However, in one embodiment they are chosen from the group of anaerobic microorganisms. In one embodiment, they are chosen from the group of carboxydotrophic acetogens.

The methods described herein before to produce the anaerobic recombinant microorganisms of other aspects of the invention, as well as methods known in the art, may be readily employed to generate the recombinant microorganisms to be selected in this aspect of the invention, adjusted to suit a particular microorganism where necessary. For example, where the microorganism is not an anaerobe, aerobic conditions can be used. The parental microorganism may be chose from any class of microorganisms, and are not limited to anaerobes. However, in one embodiment they may be chosen from the group of anaerobic microorganisms and in one particular embodiment carboxydotrophic acetogens.

Similarly, the methods for growth and fermention described for other aspects of the invention may be employed in this aspect of the invention, with conditions adjusted, as necessary for the type of microorganism of interest; for example, substituting anaerobic and aerobic conditions.

The invention also provides microorganisms cultured or grown in accordance with a method herein before described, and products produced by a method as herein before described.

EXAMPLES

The invention will now be described in more detail with reference to the following non-limiting examples.

Methods

Analysis of Vitamin Biosynthesis Pathways of *Clostridium ljungdahlii, C. autoethanogenum* and *C. ragsdalei*

The inventors analysed the genomes of the carboxydotrophic acetogens *Clostridium ljungdahlii* (NC_014328.1; Köpke et al., 2010, Proc. Nat. Acad. Sci. U.S.A., 107: 13087-13092), *C. autoethanogenum* and *C. ragsdalei*. It was found that both *C. ljungdahlii*, as well as *C. autoethanogenum* are unable to synthesize thiamine due to the lack of the thiamine biosynthesis protein ThiC that participates in the formation of 4-Amino-5-hydroxymethyl-2-methylpyrimidine from 1-(5'-Phosphoribosyl)-5-aminoimidazole ribonucleotide (AIR). ThiC is the only required gene product that has been identified for the pyrimidine biosynthesis in *E. coli, S. typhimurium*, and *B. subtilis* (Begeley et al, 1999, Arch Microbiol, 171: 293-300). On the other hand, ThiC and the full thiamine biosynthetsis pathway is present in *C. ragsdalei* and other organisms. Thiamine auxotrophy of *C. ljungdahlii* and *C. autoethanogenum* was demonstrated in serum bottle and fermentation experiments, confirming that thiamine needs to be added in fermentation medium (see below).

The panthothenate/CoA biosynthesis pathway was found to be incomplete in all three organisms, *Clostridium ljungdahlii, C. autoethanogenum* and *C. ragsdalei* due to the lack of biosynthetic genes panBCD, encoding a 3-methyl-2-oxobutanoate hydroxymethyltransferase (EC:2.1.2.11; catalyzing conversion of 5,10-Methylenetetrahydrofolate and 3-Methyl-2-oxobutanoic acid to Tetrahydrofolate and 2-Dehydropantoate), pantoate-beta-alanine ligase (EC:6.3.2.1; catalyzing the reaction of (R)-Pantoate+beta-Alanine to Diphosphate+Pantothenate), and aspartate 1-decarboxylase (EC:4.1.1.11; catalyzing the conversion of L-Aspartate to beta-Alanine).

This concept can be extended to other species of *Clostridium*, including non acetogenic Clostridial species or to other acetogenic species. Genomes can be obtained from public resources as NCBI (/genome/browse/) or KEGG (genome.jp/kegg-bin/get_htext) and then analysed for presence of genes encoding vitamin biosynthesis proteins listed in tables 1-8. For example, it was found that the genes panCD are also missing in another carboxydotrophic acetogen *Acetobacterium woodii* that has been recently sequenced (Poehlein et al., 2012) or that panBCD genes are missing in another Clostridia species as *C. phytofermentans* while all other genes of the panthothenate pathway are present.

Growth Experiments with *Clostridium ljungdahlii, C. Autoethanogenum* and *C. ragsdalei* in Media without Thiamine Experiments were performed using *C. autoethanogenum* DSM10061 and DSM23693 (a derivate of DSM10061) and *C. ljungdahlii* obtained from DSMZ (The German Collection of Microorganisms and Cell Cultures, Inhoffenstraβe 7 B, 38124 Braunschweig, Germany). *C. ragsdalei* ATCC BAA-622 was sourced from ATCC (American Type Culture Collection, Manassas, Va. 20108, USA).

All strains were cultivated at 37 C in chemically defined PETC media without yeast extract (Table 9) using strictly anaerobic conditions and techniques (Hungate, 1969, Methods in Microbiology, vol. 3B. Academic Press, New York: 117-132; Wolfe, 1971, Adv. Microb. Physiol., 6: 107-146). 30 psi carbon monioxide containing steel mill waste gas (collected from New Zealand Steel site in Glenbrook, NZ; composition: 44% CO, 32% N2, 22% $CO_2$, 2% $H_2$) served as sole carbon and energy source.

TABLE 9

PETC medium

| Media component | Concentration per 1.0 L of media |
| --- | --- |
| $NH_4Cl$ | 1 g |
| KCl | 0.1 g |
| $MgSO_4 \cdot 7H_2O$ | 0.2 g |
| NaCl | 0.8 g |
| $KH_2PO_4$ | 0.1 g |
| $CaCl_2$ | 0.02 g |
| Trace metal solution | 10 ml |
| Wolfe's vitamin solution minus Thiamine | 10 ml |
| Resazurin (2 g/L stock) | 0.5 ml |
| $NaHCO_3$ | 2 g |
| Reducing agent | 0.006-0.008% (v/v) |
| Distilled water | Up to 1 L, pH 5.5 (adjusted with HCl) |

| Wolfe's vitamin solution minus Thiamine | per L of Stock |
| --- | --- |
| Biotin | 2 mg |
| Folic acid | 2 mg |
| Pyridoxine hydrochloride | 10 mg |
| Riboflavin | 5 mg |
| Nicotinic acid | 5 mg |
| Calcium D-(+)-pantothenate | 5 mg |
| Vitamin $B_{12}$ | 0.1 mg |
| p-Aminobenzoic acid | 5 mg |
| Lipoic acid | 5 mg |
| Thiamine | 5 mg |
| Distilled water | To 1 L |

| Trace metal solution | per L of stock |
| --- | --- |
| Nitrilotriacetic Acid | 2 g |
| $MnSO_4 \cdot H_2O$ | 1 g |
| $Fe(SO_4)_2(NH_4)_2 \cdot 6H_2O$ | 0.8 g |
| $CoCl_2 \cdot 6H_2O$ | 0.2 g |
| $ZnSO_4 \cdot 7H_2O$ | 0.2 mg |
| $CuCl_2 \cdot 2H_2O$ | 0.02 g |
| $NaMoO_4 \cdot 2H_2O$ | 0.02 g |
| $Na_2SeO_3$ | 0.02 g |
| $NiCl_2 \cdot 6H_2O$ | 0.02 g |
| $Na_2WO_4 \cdot 2H_2O$ | 0.02 g |
| Distilled water | To 1 L |

| Reducing agent stock | per 100 mL of stock |
| --- | --- |
| NaOH | 0.9 g |
| Cystein•HCl | 4 g |
| $Na_2S$ | 4 g |
| Distilled water | To 100 mL |

Growth experiments were then carried out in PETC media omitting thiamine (or panthothenate) from Wolf's vitamin solution. While *C. ragsdalei* was able to grow over multiple subcultures in absence of thiamine, *C. autoethanogenum* and *C. ljungdahlii* weren't able to grow for more than 2 subculture step in absence of thiamine (or no subculture step, if the cell were washed before inoculation to remove residual thiamine), confirming the results from the genome analysis that those strains are auxotroph to thiamine.

For *C. autoethanogenum* DSM23693, also a bioreactor experiment was carried out, using a defined medium containing per liter: MgCl, $CaCl_2$ (0.5 mM), KCl (2 mM), $H_3PO_4$ (5 mM), Fe (100 µM), Ni, Zn (5 µM), Mn, B, W, Mo, Se (2 µM) was prepared for culture growth. The media was transferred into the bioreactor and autoclaved at 121° C. for 45 minutes. After autoclaving, the medium was supplemented with Wolfe's B-Vitamin solution (see above), and reduced with 3 mM Cysteine-HCl. To achieve anaerobic state, the reactor vessel was sparged with nitrogen through a 0.2 µm filter. Gas flow of carbon monioxide containing steel mill waste gas was initially set at 80 ml/min, increasing to 120 ml/min during mid exponential phase, while the agitation was increased from 250 rpm to 350. $Na_2S$ was dosed into the bioreactor at 0.25 ml/hr. Once the OD600 reached 0.4, the bioreactor was switched to a continuous mode at a rate of 1.0 ml/min (Dilution rate 0.96 $d^{-1}$). Thiamine was dosed into the reactor separately using a syringe pump. The thiamine pump was turned off for six days between day twenty and twenty six. During the period, thiamine feeding was stopped, the culture died and the biomass and gas-uptake dropped considerably. Re-starting the thiamine feeding, regenerated growth and biomass and gas uptake went back to the same level as before (FIG. 1), demonstrating that *C. autoethanogenum* is auxotroph to thiamine as expected in serum bottle experiments and from genome analysis.

Cloning of Thiamine Biosynthesis Gene thiC

The thiC gene of *Clostridium ragsdalei* was cloned into an appropriate vector for expression. Standard Recombinant DNA and molecular cloning techniques were used in this invention (Sambrook et al, Molecular Cloning: A laboratory Manual, Cold Spring Harbour Labrotary Press, Cold Spring Harbour, 1989; Ausubel et al, Current protocols in molecular biology, John Wiley & Sons, Ltd., Hoboken, 1987).

For genomic DNA extraction of *C. ragsdalei* and *C. autoethanogenum*, a 100 ml of an exponentially growing culture was harvested (4000×g, 15 min, 4° C.), washed with potassium phosphate buffer (10 mM, pH 7.5) and re-suspended in 1.9 ml STE buffer (50 mM Tris-HCl, pH 8.0, 1 mM EDTA, 200 mM sucrose). The cells were incubated for 30 minutes with 300 µL of lysozyme (100 000 U) at 37° C. The lysis step was followed by a 10 minute incubation with 10% (w/v) SDS. The RNA was digested at room temperature by adding 240 µL of 0.5 M EDTA (pH 8.0), 20 µL of 1 M Tris-HCl (pH 7.5), and 100 µL of RNase A. Then, 100 µl Proteinase K (0.5 U) were added and proteolysis took place for 3 h at 37° C. Finally, 600 µl of sodium perchlorate (5 M) were added, followed by a phenol-chloroform extraction and an isopropanol precipitation.

Figure 2:
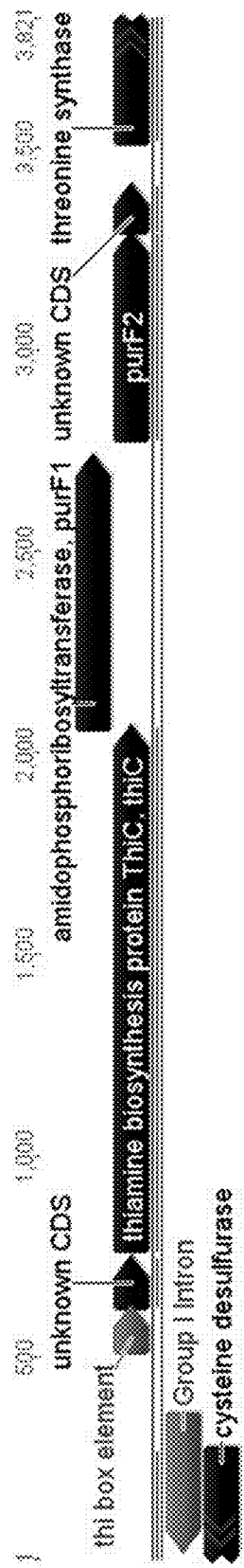
FIG. 2: Genomic arrangement of Nucleotide sequence of *C. ragsdalei* thiC/purF region, amplified by PCR.

A region (SEQ ID NO: 1) of the *C. ragsdalei* genome containing the thiC gene (SEQ ID NO: 2), as well as adjacent purF genes (SEQ ID NO: 4 and 6) encoding a amidophosphoribosyl transferase (SEQ ID NO: 5 and 7) and promoter region including regulatory thi box element (FIG. 2) using oligonucleotides ThiC-ApaI-F (SEQ ID NO: 8: GCAGGGCCCAATACGATTATCTCCTTTC) and ThiC+ PurF-Rev-SbfI (SEQ ID NO: 9: GCATCCTGCAGG-TAAATTTTGTTCTTCATT) ordered from Life Technologies. Inclusion of the PurF may not be necessary, as both *C. autoethanogenum* and *C. ljungdahlii* contain a purF gene.

The amplification was performed on an Applied Biosystems GeneAmp PCR system 9700, using iProof HF DNA polymerase (Bio-Rad) and FailSafe 2×PCR premix E buffer (Epicentre). The genes were amplified using the following program: Initial denaturation at 98° for two minutes, followed by thirty two cycles of denaturation (95° C. for 30 s), annealing (53° C. for 30 s), and extension (68° C. for 3 minutes). A final five minute extension step at 72° C. completed the amplification of the 3063 bp fragment.

Figure 3:
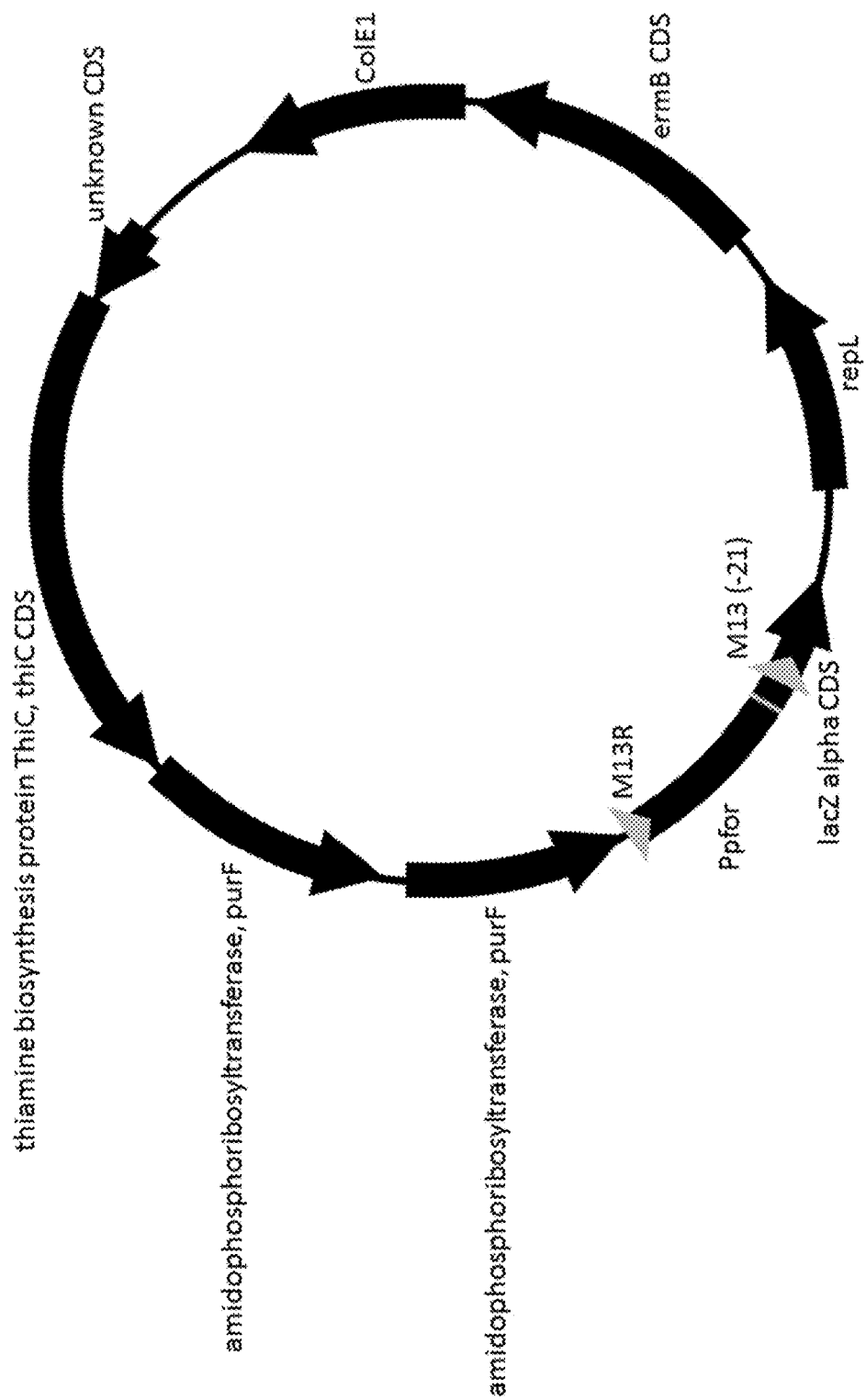
FIG. 3: Plasmid map of pMTL85246-thiC-purF.

Obtained PCR fragment was cloned into shuttle vector pMTL85246 (SEQ ID NO: 10) using ApaI and SbfI (New England Biolabs) to create plasmid pMTL85246-thiC-purF (SEQ ID NO: 11; FIG. 3). Vector pMTL85246 is a derivate of pMTL85240 with the *C. autoethanogenum* phosphotransacetylase-acetate kinase pta-ack operon promoter region (SEQ ID NO: 12) cloned in via NotI and NdeI.

The DNA fragments were incubated with ApaI and BSA at 25° C. for three hours, followed by SbfI addition and Incuabtion at 37° C. for a further three hours. A double digest at 37 C was carried out for NotI and NdeI. All Enzymes were inactivated by twenty minute incubation at 65° C. Vector pMTL85240 and pMTL85246 was dephosphorylated using Shrimp Alkaline Phosphotase (Fermentas) at 37° C. for one hour. The purified DNA fragments were ligated with T4 DNA ligase (New England Biolabs). The reaction was left to incubate at 16° C. overnight and the enzyme was inactivated with ten minute incubation at 65° C.

5 μL of the ligation mixture was transformed into electro-competent cells of a thiC negative strain of *E. coli* JW3958-1 [thiC765(del)::kan (Baba et al, 2006, *Mol. Syst. Biol.*, 2: 1-11)] obtained from the *Coli* Genetic Stock Centre (CGSC). After regeneration in LB media for 30 mins, cells were washed twice and selection was carried out using the thiC gene as selectable marker in M9 medium (Table 10) without thiamine. Colony formation took 2-3 days, and all screened colonies were positive, without any background growth. This is important when using as selectable marker and was surprisingly enabled by special treatment of cells such as washing the cells after regeneration. When expressing plant thiC gene using an antibiotic selectable marker in *E. coli*, significant background growth was observed (Kong et al., 2008, *Cell Research* 18: 566-576).

Presence of the plasmid was confirmed using colony PCR (Intron iTaq PCR premix). The PCR conditions were: 94° for three minutes, followed by thirty two cycles of denaturation (94° C. for 30 s), annealing (53° C. for 30 s), and extension (72° C. for 3 minutes). A final seven minute extension step at 72° C. completed the amplification of the 3063 bp fragment. The presence of the insert and plasmid was also confirmed using restriction digestion with NdeI (NEB) giving two bands (4269 bp and 2325 bp). The insert of the plasmid was fully sequenced to confirm sequence identity.

TABLE 10

| M9 minimal media | |
|---|---|
| Media component | Concentration per 1.0 L of media |
| M9 Salts (see below) | 200 ml |
| 1M MgSO$_4$ | 2 ml |
| 20% glucose | 20 ml |
| 1M CaCl$_2$ | 100 μl |
| Distilled water | To 1 L |
| M9 Salts | per L of Stock |
| Na$_2$HPO$_4$ | 64 g |
| KH$_2$PO$_4$ | 15 g |

TABLE 10-continued

| M9 minimal media | |
|---|---|
| NaCl | 2.5 g |
| NH$_4$Cl | 5 g |
| Distilled water | To 1 L |

Use of thiC as Selectable Marker in *C. autoethanogenum*

Prior to transformation in *C. autoethangenum*, plasmid DNA was in vivo methylated using *E. coli* strain XL1Blue MRF' and methylation plasmid pGS20 (SEQ ID NO: 13) carrying a designed methyltransferase (SEQ ID NO: 14) under control of an inducible lac promoter (SEQ ID NO: 15) as described in WO 2012/053905. Methylated plasmid DNA was purified using the PureLink™ HiPure Plasmid Purification Kit (Life Technologies). Cells were growing up in PET media (Table 9) with thiamine plus 1 g/L yeast extract and 5 g/L fructose plus steel-mill gas as carbon and energy source. A 50 mL culture of *C. autoethanogenum* DSM23693 was subcultured to fresh media for 3 consecutive days. These cells were used to inoculate 50 ml PETC media containing 40 mM DL-threonine at an OD$_{600nm}$ of 0.05. When the culture reached an OD$_{600nm}$ of 0.4, the cells were transferred into an anaerobic chamber and harvested at 4,700×g and 4° C. The culture was twice washed with ice-cold electroporation buffer (270 mM sucrose, 1 mM MgCl2, 7 mM sodium phosphate, pH 7.4) and finally suspended in a volume of 600 μl fresh electroporation buffer. This mixture was transferred into a pre-cooled electroporation cuvette with a 0.4 cm electrode gap containing 1 μg of the methylated plasmid mix and immediately pulsed using the Gene pulser Xcell electroporation system (Bio-Rad) with the following settings: 2.5 kV, 600Ω, and 25 μF. Time constants of 3.7-4.0 ms were achieved. Regeneration was carried out in 5 mL PETC media that has 10 g/L MES (2-(N-morpholino) ethanesulfonic acid) as buffer.

Cells were then either plated out on PETC-MES solid media (1.2% Bacto Agar) with thiamine and yeast extract and also 5 μg/mL clarithromycin as selectable agent, or washed twice and plated on PETC-MES solid media without yeast extract and without thiamine. In both cases, over 50 positive colonies carrying the plasmid were obtained per plate, after 3 days using clarithromycin as selectable agent and ermC as selectable marker and after 6 days on plates without yeast extract and thiamine using thiC as selectable marker.

Growth of *C. autoethanogenum* Engineered with thiC in Absence of Thiamine

Figure 5:
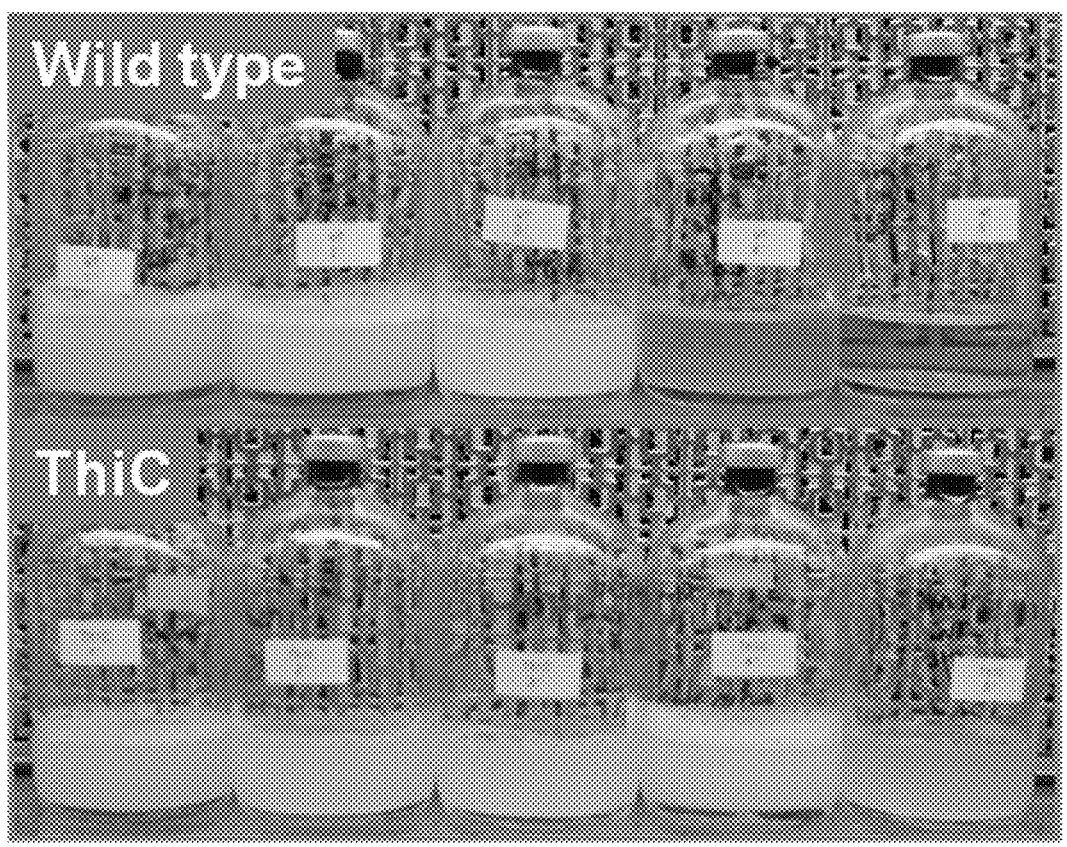
FIG. 5: Comparison of growth from *C. autoethanogenum* DSM23693 wild-type and strain carrying plasmid pMTL85246-thiC-purF in absence of thiamine.

Single colonies were picked and growth experiments were performed to compare growth in PETC media without thiamine and yeast extract and steel mill gas as sole energy and carbon source using *C. autoethanogenum* DSM23693 wild-type and strain carrying plasmid pMTL85246-thiC-purF. While growth of the wild-type ceased after two subculture steps (or within one subculture step if the cells were washed before inoculation), the strain carrying plasmid pMTL85246-thiC-purF was able to grow sustainable for multiple subculturing steps (regardless if the cells have been washed or not) (FIG. 5). Experiments were carried out in triplicates using in serum bottles and a volume of 50 mL. The presence of plasmid was checked by PCR.

This demonstrates that the organism is able to synthesize thiamine by itself and thiC can be used as selectable marker in carboxydotrophic acetogen *C. autoethanogenum*.

Use of panBCD as Selectable Marker

The inventors have identified that C. autoethanogenus, C. ljungdahlii and C. ragsdalei have an incomplete panthothenate pathway lacking biosynthetic genes panBCD, encoding a 3-methyl-2-oxobutanoate hydroxymethyltransferase (EC:2.1.2.11; catalyzing conversion of 5,10-Methylenetetrahydrofolate and 3-Methyl-2-oxobutanoic acid to Tetrahydrofolate and 2-Dehydropantoate), pantoate-beta-alanine ligase (EC:6.3.2.1; catalyzing the reaction of (R)-Pantoate+ beta-Alanine to Diphosphate+Pantothenate), and aspartate 1-decarboxylase (EC:4.1.1.11; catalyzing the conversion of L-Aspartate to beta-Alanine). In other acetogens such as Acetobacterium woodii, whose genome (Poehlein et al, 2012, PLoS One 7: e33439), genes panB and panC were also found to be absent, while the rest of the panthothenate biosynthesis pathway is present.

Figure 4:
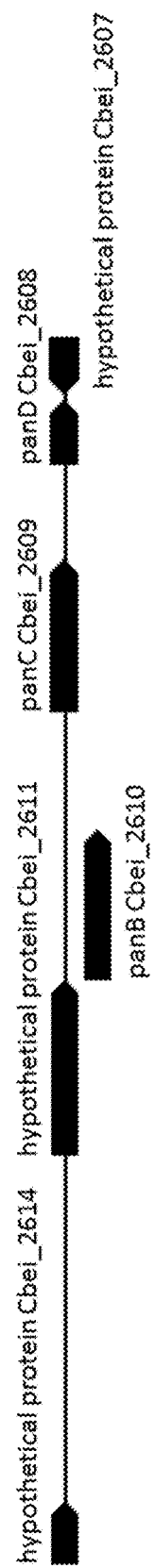
FIG. 4: Genomic arrangement of Nucleotide sequence of *C. beijerickii* panBCD operon.

The same principle as for thiC and thiamine as selectable marker and agent may be applied for panBCD and panthothenate in these organisms. While in case of thiC only one gene is required, here three genes are missing. However, all three genes have been found to be organized in one cluster in for example C. beijerinckii (FIG. 4). This cluster (NC_009617.1, 3038300-3034200) including promoter regions and genes panB (Cbei_2610; Gene ID: 5293811; YP_001309722.1), panC (Cbei_2609; Gene ID: 5293810; YP_001309721.1), and panD (Cbei_2608; Gene ID: 5293809; YP_001309720.1) may be amplified from genomic DNA of C. beijerinckii by PCR and cloned into an expression vector as described for the thiC gene from C. ragsdalei. This construct could then be used in a similar fashion as described for the thiC construct by omitting panthothenate instead of thiamine for expression in a organism lacking any of these genes, such as carboxydotrophic acetogens C. autoethanogenum, C. ljungdahlii, A. woodii, and C. ragsdalei or a panBCD negative strain of E. coli like E. coli JW0129-1 (panC750(del)::kan), JW0130-1 (panB751(del)::kan), and JW0127-2 (panD748(del)::kan) (Baba et al, 2006, Mol. Syst. Biol., 2: 1-11) which can be obtained from the Coli Genetic Stock Centre (CGSC).

Cloning of panBCD panBCD genes were cloned into an expression vector using GeneArt Seamless Cloning and Assembly kit (Life Technologies). Large PCR primers containing a 20 bp overhang homology to the desired vector were designed.

| Primer | sequence |
|---|---|
| panBCD-83155-F1 | AGGAAATGAACATGAAACATGTGAAAAATACAGTATTAACTT TTAAACAAG (SEQ ID NO: 16) |
| panBCD-GeneD-R1 | GACGTCGACTCTAGAGGATCTTATTCATTTGATTCATAATTA GTTATTTCTTTTATTG (SEQ ID NO: 17) |

The panBCD sequence was PCR amplified using iProof high fidelity DNA polymerase from C. beijerinckii. The protocol to amplify the 2813 bp fragment was: Initialisation 30 s, Danturation 10 s, annealing 30 s, Extension 2 minutes, and a final extension step of 7 minutes.

The DNA was purified using DNA Clean and Concentrator-5 (Zymo Research). pMTL vector 83155 carrying the catP antibiotic resistance marker along with the Ppta promoter was digested using NdeI and BamHI (Fermentas) and purified using DNA Clean and Concentrator-5 (Zymo Research). 100 ng of the digested vector was mixed with a 2:1 molar ratio of insert, along with 5× reaction buffer and 10× Enzyme mix. The mixture was incubated at room temperature for 30 minutes and immediately transformed into One Shot TOP10 E. coli competent cells. 50 µL of transformed E. coli was spread on LB agar plates containing 5 µg/ml chloramphenicol. Four colonies were screened using iNtron Maxime PCR PreMix i-MAX II (Tech Dragon Limited) from an overnight incubation

| Primer | sequence |
|---|---|
| M13F | TGTAAAACGACGGCCAGT (SEQ ID NO: 18) |
| M13 R | CAGGAAACAGCTATGACC (SEQ ID NO: 19) |

The protocol to amplify the 3404 bp fragment was: Initialisation 30 s, Danturation 10 s, annealing 30 s, Extension 2 minutes, and a final extension step of 7 minutes.

The four plasmids were further checked by restriction digests using NotI and EcoRV (fermentas). Expected sizes from digestion: 2343 bp and 5383 bp, undigested plasmid: 7726 bp The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. Titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as, an acknowledgment or any form of suggestion that they constitute valid prior art or form part of the common general knowledge in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

The invention claimed is:

1. A method of using vitamin prototrophy as a selectable marker comprising:
   (a) transforming a microorganism auxotrophic for a vitamin with both a vitamin biosynthesis gene and a gene conferring a desired property, wherein the microorganism is not transformed with an antibiotic resistance gene and
   (b) culturing the microorganism in the absence of the vitamin,
   wherein growth of the microorganism in the absence of the vitamin indicates successful transformation of the microorganism with both the vitamin biosynthesis gene and the gene conferring a desired property,
   wherein the vitamin is thiamine, the vitamin biosynthesis gene encodes thiamine biosynthesis protein (ThiC) (EC 4.1.99.17) derived from *Clostridium ragsdalei*, and the microorganism is *Clostridium autoethanogenum*.

2. The method of claim 1, wherein the culturing is performed in the absence of an antibiotic.

3. The method of claim 1, wherein antibiotic resistance is not used as a selectable marker.

4. The method of claim 1, wherein transformation with the vitamin biosynthesis gene renders the microorganism prototrophic for the vitamin.

5. The method of claim 1, wherein the gene conferring the desired property is not an antibiotic resistance gene, an auxotrophic marker, or a reporter gene.

6. The method of claim 1, wherein the microorganism is further transformed with a second vitamin biosynthesis gene encoding methyl-2-oxobutanoate hydroxymethyltransferase (PanB) (EC 2.1.2.11), pantoate-beta-alanine ligase (PanC) (EC 6.3.2.1), and aspartate 1-decarboxylase (PanD) (EC 4.1.1.11).

7. The method of claim 6, wherein the second vitamin biosynthesis gene is panBCD derived from *Clostridium beijerinckii*.

8. The method of claim 1, wherein the method is used to select against an undesirable or contaminating microorganism that is auxotrophic for the vitamin.

* * * * *